(12) United States Patent
Ramos et al.

(10) Patent No.: US 11,944,612 B2
(45) Date of Patent: *Apr. 2, 2024

(54) DOSING REGIMENS FOR 2-HYDROXY-6-((2-(1-ISOPROPYL-1H-PYRAZOL-5-YL)PYRIDIN-3-YL)METHOXY) BENZALDEHYDE

(71) Applicant: Global Blood Therapeutics, Inc., South San Francisco, CA (US)

(72) Inventors: Eleanor L. Ramos, South San Francisco, CA (US); Joshua Eli Lehrer-Graiwer, South San Francisco, CA (US); Athiwat Hutchaleelaha, South San Francisco, CA (US); Naveen Bejugam, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,874

(22) Filed: Aug. 5, 2022

(65) Prior Publication Data

US 2022/0378770 A1 Dec. 1, 2022

Related U.S. Application Data

(63) Continuation of application No. 17/559,156, filed on Dec. 22, 2021, now abandoned, which is a continuation of application No. 17/326,045, filed on May 20, 2021, now abandoned, which is a continuation of application No. 15/368,142, filed on Dec. 2, 2016, now Pat. No. 11,020,382.

(60) Provisional application No. 62/375,832, filed on Aug. 16, 2016, provisional application No. 62/263,554, filed on Dec. 4, 2015.

(51) Int. Cl.
*A61K 31/4439* (2006.01)
*A61K 9/16* (2006.01)
*A61K 9/48* (2006.01)

(52) U.S. Cl.
CPC ........ *A61K 31/4439* (2013.01); *A61K 9/1605* (2013.01); *A61K 9/4858* (2013.01); *A61K 9/4866* (2013.01)

(58) Field of Classification Search
CPC .............. A61K 31/4439; A61K 9/1605; A61K 9/4858; A61K 9/4866; A61P 35/02
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 10/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greewald et al. |
| 6,627,646 B2 | 9/2003 | Bakale |
| 6,630,496 B1 | 10/2003 | Seehra et al. |
| 7,160,910 B2 | 1/2007 | Safo et al. |
| 7,411,083 B2 | 8/2008 | Gopalsamy et al. |
| 7,994,367 B2 | 8/2011 | Nakazawa |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,150,569 B2 | 10/2015 | Fukuda et al. |
| 9,248,199 B2 | 2/2016 | Metcalf et al. |
| 9,422,279 B2 | 8/2016 | Metcalf et al. |

(Continued)

FOREIGN PATENT DOCUMENTS

| | | |
|---|---|---|
| CA | 2720096 | 10/2015 |
| CN | 101113148 | 1/2008 |

(Continued)

OTHER PUBLICATIONS

US 10,450,268 B2, 10/2019, Xu et al. (withdrawn)

(Continued)

*Primary Examiner* — Jean P Cornet

(57) ABSTRACT

Provided herein are methods for treating sickle cell disease, comprising administering to a subject 2-hydroxy-6-((2-(1-isopropyl-1H-pyrazol-5-yl)pyridin-3-yl)-methoxy)benzaldehyde (Compound 1), or a polymorph thereof, in certain dosing regimens.

23 Claims, 10 Drawing Sheets

(56) References Cited

U.S. PATENT DOCUMENTS

| | | |
|---|---|---|
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,990 B2 | 10/2017 | Li et al. |
| 9,957,250 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,137,118 B2 | 11/2018 | Li et al. |
| 10,683,285 B2 | 6/2020 | Li et al. |
| 2001/0046997 A1 | 11/2001 | Abraham et al. |
| 2002/0022923 A1 | 2/2002 | Hirabayashi et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0015752 A1 | 1/2007 | Hangauer |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yanaguchi et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0292513 A1 | 11/2010 | Nakazawa |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf |
| 2013/0190316 A1 | 7/2013 | Metcalf et al. |
| 2013/0190375 A1 | 7/2013 | Dunkel et al. |
| 2013/0273157 A1 | 10/2013 | Ishi et al. |
| 2014/0004184 A1 | 1/2014 | Ashraf et al. |
| 2014/0142149 A1 | 5/2014 | Zhang et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0225366 A1 | 8/2015 | Li |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344473 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Shiha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0355713 A1 | 12/2017 | Harris et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |
| 2019/0202782 A1 | 7/2019 | Xu et al. |
| 2019/0255031 A1 | 8/2019 | Li et al. |
| 2020/0048280 A1 | 2/2020 | Li et al. |
| 2020/0079732 A1 | 3/2020 | Xu et al. |
| 2020/0140384 A1 | 5/2020 | Metcalf et al. |
| 2020/0190058 A1 | 6/2020 | Metcalf et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| DE | 258226 | 7/1998 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |
| GB | 1409865 | 10/1975 |
| GB | 1593417 | 7/1981 |
| IL | 64573 | 4/1985 |
| JP | 57145844 | 6/1905 |
| JP | 59029667 | 2/1984 |
| JP | 61040236 | 2/1986 |
| JP | 63230687 | 9/1988 |
| JP | 63258463 | 10/1988 |
| JP | 01190688 | 7/1989 |

(56) References Cited

FOREIGN PATENT DOCUMENTS

| | | |
|---|---|---|
| JP | 06041118 | 2/1994 |
| JP | 07025882 | 1/1995 |
| JP | 2002523469 | 7/2002 |
| JP | 2002528537 | 9/2002 |
| JP | 2003075970 | 3/2003 |
| JP | 2003513060 | 4/2003 |
| JP | 2006342115 | 12/2006 |
| JP | 2009203230 | 9/2009 |
| TW | 201612717 | 4/2016 |
| WO | 199119697 | 12/1991 |
| WO | 199202503 | 2/1992 |
| WO | 199317013 | 9/1993 |
| WO | 199401406 | 1/1994 |
| WO | 199514015 | 5/1995 |
| WO | 199521854 | 8/1995 |
| WO | 199611902 | 4/1996 |
| WO | 199741120 | 11/1997 |
| WO | 199744306 | 11/1997 |
| WO | 199808818 | 3/1998 |
| WO | 199809967 | 3/1998 |
| WO | 199821199 | 5/1998 |
| WO | 199929694 | 6/1999 |
| WO | 199943672 | 9/1999 |
| WO | 199947529 | 9/1999 |
| WO | 199948490 | 9/1999 |
| WO | 199959978 | 11/1999 |
| WO | 199962908 | 12/1999 |
| WO | 200012121 | 3/2000 |
| WO | 200026202 | 5/2000 |
| WO | 200035858 | 6/2000 |
| WO | 200040564 | 7/2000 |
| WO | 200071123 | 11/2000 |
| WO | 200075145 | 12/2000 |
| WO | 200078746 | 12/2000 |
| WO | 200100612 | 1/2001 |
| WO | 200119823 | 3/2001 |
| WO | 200123383 | 4/2001 |
| WO | 200132596 | 5/2001 |
| WO | 200136375 | 5/2001 |
| WO | 200151919 | 7/2001 |
| WO | 200157006 | 8/2001 |
| WO | 200157044 | 8/2001 |
| WO | 200162705 | 8/2001 |
| WO | 200170663 | 9/2001 |
| WO | 2002000622 | 1/2002 |
| WO | 200212235 | 2/2002 |
| WO | 200224635 | 3/2002 |
| WO | 200224679 | 3/2002 |
| WO | 200240456 | 5/2002 |
| WO | 2003048132 | 6/2002 |
| WO | 200251849 | 7/2002 |
| WO | 2002051849 | 7/2002 |
| WO | 2002053547 | 7/2002 |
| WO | 2003051366 | 6/2003 |
| WO | 2003053368 | 7/2003 |
| WO | 2003101959 | 12/2003 |
| WO | 2004014899 | 2/2004 |
| WO | 2004018430 | 3/2004 |
| WO | 2004024705 | 3/2004 |
| WO | 200450030 | 6/2004 |
| WO | 2004056727 | 7/2004 |
| WO | 2004058790 | 7/2004 |
| WO | 2004073675 | 9/2004 |
| WO | 2004087075 | 10/2004 |
| WO | 2004111031 | 12/2004 |
| WO | 2005047249 | 5/2005 |
| WO | 2005074513 | 8/2005 |
| WO | 2005077932 | 8/2005 |
| WO | 2005086951 | 9/2005 |
| WO | 2005087766 | 9/2005 |
| WO | 2005096337 | 10/2005 |
| WO | 2006011469 | 2/2006 |
| WO | 2006065204 | 6/2006 |
| WO | 2006088173 | 8/2006 |
| WO | 2006101318 | 9/2006 |
| WO | 2006101321 | 9/2006 |
| WO | 2006103463 | 10/2006 |
| WO | 2006116764 | 11/2006 |
| WO | 2006003923 | 12/2006 |
| WO | 2006106711 | 12/2006 |
| WO | 2007003962 | 1/2007 |
| WO | 2007009389 | 1/2007 |
| WO | 2007017267 | 2/2007 |
| WO | 2007047204 | 4/2007 |
| WO | 2007049675 | 5/2007 |
| WO | 2007061923 | 5/2007 |
| WO | 2007084914 | 7/2007 |
| WO | 2007095495 | 8/2007 |
| WO | 2007117180 | 10/2007 |
| WO | 2008012495 | 1/2008 |
| WO | 2008013414 | 1/2008 |
| WO | 2008016132 | 2/2008 |
| WO | 2008029200 | 3/2008 |
| WO | 2008041118 | 4/2008 |
| WO | 2008051532 | 5/2008 |
| WO | 2008060391 | 5/2008 |
| WO | 2008066145 | 6/2008 |
| WO | 2008081096 | 7/2008 |
| WO | 2008101682 | 8/2008 |
| WO | 2008116620 | 10/2008 |
| WO | 2009001214 | 12/2008 |
| WO | 2009011850 | 1/2009 |
| WO | 2009050183 | 4/2009 |
| WO | 2009125606 | 10/2009 |
| WO | 2009128537 | 10/2009 |
| WO | 2009130560 | 10/2009 |
| WO | 2009436889 | 11/2009 |
| WO | 2009146555 | 12/2009 |
| WO | 2009153191 | 12/2009 |
| WO | 2010031589 | 3/2010 |
| WO | 2010056631 | 5/2010 |
| WO | 2010129055 | 11/2010 |
| WO | 2011033045 | 3/2011 |
| WO | 2011088201 | 7/2011 |
| WO | 2011136459 | 11/2011 |
| WO | 2012020060 | 2/2012 |
| WO | 2012138981 | 10/2012 |
| WO | 2012141228 | 10/2012 |
| WO | 2013052803 | 4/2013 |
| WO | 2013102142 | 7/2013 |
| WO | 2013102145 | 7/2013 |
| WO | 2014104384 | 7/2014 |
| WO | 2014150256 | 9/2014 |
| WO | 2014150258 | 9/2014 |
| WO | 2014150261 | 9/2014 |
| WO | 2014150268 | 9/2014 |
| WO | 2014150276 | 9/2014 |
| WO | 2014150289 | 9/2014 |
| WO | 2015031284 | 3/2015 |
| WO | 2015031285 | 3/2015 |
| WO | 2015116061 | 8/2015 |
| WO | 2015120133 | 8/2015 |
| WO | 2016043849 | 3/2016 |
| WO | 2016160755 | 10/2016 |
| WO | 2017096230 | 6/2017 |

OTHER PUBLICATIONS

Vichinsky, et al., "A Phase 3 Randomized Trial of Voxelotor in Sickle Cell Disease", New England Journal of Medicine, 2019, pp. 509-519, 381(6).

Vippagunta, et al., "Crystalline Solids", Advanced Drug Delivery Reviews, 2001, pp. 3-26, vol. 48.

Wang, et al., "Studies of Benzothiophene Template as Potent Factor Ixa (FIXa) Inhibitors in Thrombosis", Journal of Medicinal Chemistry, 2010, pp. 1465-1472, vol. 53.

Warshawsky, et al., "The synthesis of aminobenzazespinones as anti-phenylalanine dipeptide mimics and their use in NEP inhibition", Bioorganic & Medicinal Chemistry Letter, 1996, pp. 957-962, 6(8).

Wendt, et al., "Synthesis and SAR of 2-arly pyrido[2,3-d]pyrimidines as potent mGlu5 receptor antagonists", Bioorganic &

(56) References Cited

OTHER PUBLICATIONS

Medicinal Chemistry Letters, Pergamon, Amsterdam, NL, Sep. 15, 2007, pp. 5396-5399, 17(19).
Wermuth, Camille G., "Molecular Variations Based on Isosteric Replacements", The Practice of Medicinal Chemistry, 1996, pp. 203-232.
Wong, et al., "Renal failure in sickle cell anemia", Hematol Oncol Clin North Am., Dec. 1996, pp. 1321-1331, 10(6).
Yamano, Mitsuhisa, "Approach to Crystal Polymorphs in Process Research of New Drug", Journal of Synthetic Organic Chemistry, Japan, 2007, pp. 907-913, 65(9), (in Japanese with partial English translation).
Yan, et al., "Synthesis, crystal structure and antibacterial activity of dibutylitin carboxylate", Huaxue Tongbao, 2007, pp. 313-316, 70(4).
Yan, et al., "Synthesis, crystal structure and antibacterial activity of di-n-butyltin di-2(2-formylphenoxy)acetic ester", Yingyong Huaxue, 2007, pp. 660-664, 24(6).
Yang, et al., "Structural requirement of chalcones for the inhibitory activity of interleukin-5", Bioorganic Medicinal Chemistry, Jan. 1, 2007, pp. 104-111, 15(1)., Epub Oct. 10, 2006.
Yoon, et al., "The Chirality Conversion Reagent for Amino Acids Based on Salicyl Aldehyde", Bull. Korean Chem. Soc., 2012, pp. 1715-1718, vol. 33.
Zhang, et al., "A selective fluorescent chemosensor with 1, 2, 4-triazole as subunit for Cu (II) and its application in maging Cu (II) in living cells", Dyes and Pigments, 2012, pp. 1370-1375, 92(3).
Zhang, et al., "Current prodrug strategies for improving oral absorption of nucleoside analogues", Asian Journal of Pharmaceutical Sciences, Apr. 2014, pp. 65-74, 9(2).
Zhang, et al., "DFT study on RuII-catalyzed cyclization of terminal alkynals to cycloalkenes", International Journal of Quantum Chemistry, 2009, pp. 679-687, 109(4).
Zhu, et al., "Isoquinoline-pyridine-based protein kinase B/Akt antagonists: SAR and in vivo antitumor activity", Bioorganic & Medicinal Chemistry Letters, Pergamon, Amsterdam, NL, 2006, pp. 3150-3155, 16(12).
Zwaagstra, et al., "Synthesis and Structure-Activity Relationships of Carboxylated Chalcones: A Novel Series of Cys-LT1 (LTD4) Receptor Antagonists", Journal of Medicinal Chemistry, 1997, pp. 1075-1089, 40(7).
U.S. Pharmacopia #23, National Formulary #18, 1995, pp. 1843-1844.
U.S. Appl. No. 61/581,053, filed Dec. 28, 2011, Metcalf et al.
U.S. Appl. No. 61/661,320, filed Jun. 18, 2012, Metcalf et al.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
"Can Voxelotor Offer New HOPE for Sickle Cell Disease?," Dec. 3, 2018, available at: https://www.ashclinicalnews.org/on-location/voxelotor-offers-new-hope-sickle-cell-disease/. 4 pages.
Abdulmalik, et al., "Crystallographic analysis of human hemoglobin elucidates the structural basis of the potent and dual antisickling activity of pyridyl derivatives of vanillin" Acta Cryst., 2011, pp. 920-928, D67.
Abdulmalik, et al., "Sickle cell disease: current therapeutic approaches", Expert Opinion of Therapeutic Patents, 2005, pp. 1497-1506, 15(11).
Abraham, et al., "Vanillin, a Potential Agent for the Treatment of Sickle Cell Anemia", Blood, Mar. 1991, pp. 1334-1341, 77(6).
Adhikary, P.K., et al., "A new antisickling agent: In vitro studies of its effect on S/S erythrocytes and on hemoglobin S", Experientia, 1978, pp. 804-806, 34(6).
Appendix A provided with Israel office action dated Aug. 11, 2016, for IL 233329.
Arya, R., et al., "Tucaresol increases oxygen affinity and reduces haemolysis in subjects with sickle cell anaemia", British Journal Haematology, 1996, pp. 817-821, 93(4).
Ashizawa et al., "Polymorphism and crystallization of the pharmaceutical drugs", (Iyakuhin No Takeigensho to Shoseki No Kagaku) Maruzen Planet Co., Ltd., Sep. 20, 2002, pp. 3-16 and pp. 273-278. (in Japanese with partial English translation).
Australian Examination Report dated Nov. 7, 2016, for AU 2016203755.
Babu, et al., "Regioselective synthesis and structural elucidation of 1,4-disubstituted 1,2,3-traizole derivatives using 1D and 2D NMR spectral techniques", Magn. Reson. Chem., 2011, pp. 824-829, vol. 49, doi:10:1002/mrc.2820.
Bacsa, et al., "Novel products from Baylis-Hillman reactions of salicylaldehydes", South African Journal of Chemistry, 1998, pp. 47-54, 51(1), CODEN: SAJCDG; ISSN: 0379-4350.
Ballerini, et al., "High pressure Diels-Alder approach to hydroxy-substituted 6a-cyano-tetrahydro-6H-benzo[c]chromen-6-ones: A route to Δ6-Cis-Cannabidiol", Journal of Organic Chemistry, 2009, pp. 4311-4317, 74(11).
Ballet, et al., "Novel selective human melanocortin-3 receptor ligands: Use of the 4-amino-1,2-4,5-tetrahydro-2-benzazepin-3-one (Aba) scaffold", Bioorganic and Medicinal Chemistry Letters, 2007, pp. 2492-2498, 17(9), CODEN; BMCLES; ISSN: 0960-894X.
Barnes, "COPD: is there light at the end of the tunnel?", Current Opinion in Pharmacology, 2004, pp. 263-272, vol. 4.
Barnes, et al., "Prospects for new drugs for chronic obstructive pulmonary disease", The Lancet, 2004, pp. 985-996, vol. 364.
Baxter, et al., "Reductive aminations of carbonyl compounds with borohydride and borane reducing agents", Organic Reactions (Hoboken, NJ, United States), 2002, 59, no page given bin/mrwhome/107610747/HOME.
Beaumont, et al., "Design of ester prodrugs to enhance oral absorption of poorly permeable compounds: Challenges to the discovery scientist", Current Drug Metabolism, 2003, pp. 461-485, vol. 4.
Beddell, "Substituted benzaldehydes designed to increase the oxygen affinity of human haemoglobin and inhibit the sickling of sickle erythrocycles", British Journal of Pharmac., 1984, pp. 397-407, vol. 82.
Beena, et al., "Synthesis and antibacterial activity evaluation of metronidazole-triazole conjugates", Bioorganic & Medicinal Chemistry Letters, 2009, pp. 1396-1398, 19(5).
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
Berge, et al., "Pharmaceutical Salts", Journal of Pharmaceutical Science, 1977, pp. 1-19, vol. 66.
Beringer et al., Remington's Pharmaceutical Sciences, Mack Pub., 21st Edition, 2005, pp. 1072-1076.
Berstein, "Crystals in Supramolecular Chemistry", ACA Transactions, 2004, pp. 1-14, vol. 39.
Berstein, "Polymorphism in Molecular Crystals", Clarendon Press, Oxford, 2002, pp. 115-118, vol. 272.
Bode, et al., "Novel synthesis and x-ray crystal structure of a coumarin derivative", South African Journal of Chemistry, 1992, pp. 25-27, 45(1), Coden; SAJCDG; ISSN: 0379-4350.
Bonaventura, et al., "Molecular Controls of the Oxygenation and Redox Reactions of Hemoglobin", Antioxidants & Redox Signaling, 2013, pp. 2298-2313, 18(17).
Bottino, et al., "Study on the scope of tert-amino effect: new extensions of type 2 reactions to bridged biaryls", J. Phys. Org. Chem., 2012, pp. 1033-1041, 25(11).
Bradbury, et al., "New nonpeptide angiotensin II receptor antagonists", Journal of Medicinal Chemistry, 1993, pp. 1245-1254, vol. 36.
Braga, et al., "Making crystals from crystals: a green route to crystal engineering and polymorphism", Chem Commun (Camb), Aug. 2005, pp. 3635-3645, vol. 29, Epub Jun. 15, 2005.
Britton, et al., "Structure-activity relationships of a series of benzothlophens-derived NPY Y1 antagonists: optimization of the C-2 side chain", Bioorganic & Medicinal Chemistry Letters, 1999, pp. 475-480, 9(3). CODEN: BMCLE8; ISSN: 0960-894X.
Brown, et al., "1,2-Dihydroisoquinollnes. III, Dimerization", Tetrahedron, 1966, pp. 2437-2443, 22(8), CODEN: TETRAB; ISSN: 0040-4020.
Byrn, et al., "Pharmaceutical solids: a strategic approach to regulatory considerations", Pharmaceutical Research. 1995; 12(7):945-954.

(56) References Cited

OTHER PUBLICATIONS

Caira, "Crystalline Polymorphism of Organic Compounds", Topics in Current Chemistry, Springer, Berlin DE, 1998, pp. 163-208, vol. 198.
CAS Reg. No. 921186-17-6, entered into STN on Feb. 15, 2007.
CAS Registry No. 1039841-20-7, entry dated Aug. 10, 2008.
CAS Registry No. 1096911-11-3, entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 329222-79-.9; STN Entry Date Mar. 28, 2001; Benzaldehyde, 2-[(4-chloro-3-methylphenoxy)methyl]-4-methoxy.
CAS Registry No. 631858-40-7; entry dated Dec. 29, 2003.
CAS Registry No. 733030-49-4; STN Entry Date Aug. 26, 2004; Benzaldehyde, 5-bromo-2-)phenoxymethyl)-.
CAS Registry No. 886362-88-5; STN Entry Date Jun. 1, 2006; Benzaldehyde, 2,4-dichloro-6-[(4-fluorophenoxy)methyl}-.
CAS Registry No. 921186-17-6, entered into STN on , Feb. 15, 2007.
Chemical Abstract Registry No. 1142191-55-6, indexed in the Registry file on STN CA ONINE, May 4, 2009.
Cheng, et al., "Vilsmeier formylation of tert-anilines: dibenzo[b,f][1,5]diazocines and quinazolinium salts via the 't-amino effect'1." Journal of Chemical Society, Perkin Trans 1, 1998, pp. 1257-1262.
Cherian, et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine(6-AminoPA-824)", Journal of Medicinal Chemistry, Aug. 2011, pp. 5639-5959, 54(16).
Handbook of Pharmaceutical Excipients, Fifth Ed., Edited by Raymond C. Rowe, et al., ISBN 978-0-85369-618-6, pp. 132-134, 211-213, 346-347, 389-394, 430-433, Dec. 31, 2006.
Hang, Song. "Pharmaceutical Separation Engineering" East China University of Technology Press. Aug. 31, 2011; 270-272. (in Chinese with English abstract).
Hanmantgad, et al., "Synthesis and pharmacological properties of some r-(2-benzo[b]furanyl)coumarins", Indian Journal of Chemistry, Section B., Organic Chemistry Including Medicinal Chemistry, 1996, pp. 779-781, 25B(7), CODEN: IJSBDB; ISSN: 0376-4699.
He, et al., "Prodrugs of Phosphonates, Phosphinates, and Phosphates", Prodrugs: Challenges and rewards Part 2, edited by Stella, et al., 2007, pp. 223-264.
Hebbel, et al., "Sickle hemoglobin oxygen affinity-shifting strategies have unequial cerebrovascular risks", Am. J. Hematol., 2018, pp. 321-325, 93(3).
Heimbach, et al., "Enzyme-mediated precipitation of patent drugs from their phosphate prodrugs", International Journal of Pharmaceutics, 2003, pp. 81-92, vol. 261.
Heimbach, et al., "Prodrugs: Challenges and Rewards Part I", New York, NY, Singer: AAPS Press, 2007, 5(Chapter 2.2.1): 157-215 Overcoming Poor Aquenous Solubility for Oral Delivery.
Heimgartner, et al., "Stereoselective synthesis of swainsonines from pyridines", Tetrahedron, Elsevier Science Publisher, Amsterdam, NL, 2005, pp. 643-655, 61(3).
Hoffman, et al., 3-Hydroxy-3-methyglutaryl-coenzyme A Reductase Inhibitors, 2, Structural Modification of 7-(Substituted aryl)-3, 5-dihydroxy-6-heptenoic Acids and Their Lactone Derivatives, Journal of Medical Chemistry, 1986, pp. 159-169, 29(2).
Hong, et al., "Potential Anticancer Agents VI: 5-Substituted Pyrimidine-6-Carboxaldehydes", Journal of Pharmacetical Sciences, American Pharmaceutical Associations, Washington, US, 1970, pp. 1637-1645, 59(11).
Huckauf, et al., "Oxygen Affinity of Haemoglobin and Red Cell Acid-Base Status in Patients with Severe Chronic Obstructive Lung Disease", Bull. Europe Physiopath. Resp., 1976, pp. 129-142, vol. 12.
Hutchaleelaha, et al., "Pharmacokinetics and pharmacodynamics of voxelotor (GBT440) in healthy adults and patients with sickle cell disease", British Journal of Clinical Pharmacology, Jun. 2019, pp. 1290-1302, 85(6).
International Patent Application No. PCT/US2016/064723, Search Report and Written Opinion, dated May 3, 2017, 15 pages, (WO 2017/096230).
International Preliminary Report on Patentability for Patent Application No. PCT/US2014/0022742 dated Sep. 15, 2015, 7 pages.
International Preliminary Report on Patentability for Patent Application No. PCT/US2014/022733 dated Sep. 15, 2015, 11 pages.
International Preliminary Report on Patentability for Patent Application No. PCT/US2014/022769 dated Sep. 15, 2015, 8 pages.
International Preliminary Report on Patentability for Patent Application No. PCT/US2016/064723, dated Jun. 5, 2018, 10 pages, (WO 2017/096230).
International Preliminary Report on Patentability for Patent Application No. PCT/US2014/022846 dated Sep. 15, 2015, 7 pages.
International Search Report and Written Opinion dated Aug. 19, 2014, for PCT Application No. PCT/US2014/022736, 14 pages.
International Search Report and Written Opinion dated Aug. 27, 2014, for PCT Application No. PCT/US2014/022742, 11 pages.
International Search Report and Written Opinion dated Dec. 8, 2014, for PCT Application No. PCT/US2014/050575, 10 pages.
International Search Report and Written Opinion dated Jan. 2, 2020, for PCT Application No. PCT/US2019/053862, 13 pages.
International Search Report and Written Opinion dated Jan. 22, 2018, for PCT Application No. PCT/US2017/056352, 12 pages, published-WO 2018071678.
International Search Report and Written Opinion dated Jul. 22, 2014, for PCT Application No. PCT/US2014/022846, 11 pages.
International Search Report and Written Opinion dated Jul. 30, 2014, for PCT Application No. PCT/US2014/029682, 16 pages.
International Search Report and Written Opinion dated Jul. 31, 2014, for PCT Application No. PCT/US2014/022789, 13 pages.
International Search Report and Written Opinion dated Jul. 4, 2014, for PCT Application No. PCT/US2014/022769, 11 pages.
International Search Report and Written Opinion dated Mar. 5, 2013 for PCT Application No. PCT/US2012/072177, 7 pages.
International Search Report and Written Opinion dated Mar. 5, 2021, for PCT Application No. PCT/US2020/060923, 13 pages.
International Search Report and Written Opinion dated May 11, 2015, for PCT Application No. PCT/US2015/014589, 5 pages.
International Search Report and Written Opinion dated May 20, 2013, for PCT Application No. PCT/US2012/072183, 11 pages.
International Search Report and Written Opinion dated Nov. 28, 2014, for PCT Application No. PCT/US2014/052576, 10 pages.
International Search Report and Written Opinion dated Oct. 31, 2014, for PCT Application No. PCT/US2014/013575, 10 pages.
International Search Report and Written Opinion for PCT/US2017/032104, dated Aug. 4, 2017, 10 pages.
Israel office action dated Aug. 11, 2016, for Israeli Patent Application No. 233329.
Ito et al., "A medium-term rat liver bioassay for rapid in vivo detection of carcinogenic potential of chemicals, 01D", Cancer Science, Jan. 2003, pp. 3-8, vol. 94.
Ivanisevic, et al., "Uses of x-ray powder diffraction in the pharmaceutical industry", Pharm Sci. Encycl, 2010, pp. 1-42.
Jain, et al., "Polymorphism in Pharmacy", Indian Drugs, 1986, pp. 315-329, 23(6).
Jarvest, et al., "Discovery and optimisation of potent, selective, ethanolamine Inhibitors of bacterial phenylalanyl tRNA synthetase", Bioorganic & Medicinal Chemistry Letter, 2005, pp. 2305-2309, 15(9).
Karche, et al., "Electronic Effects in Migratory Groups [1,4]-versus [1,2]-Rearrangement in Rhodium Carbenoid Generated Bicyclic Oxonium Ylides", Journal of Organic Chemistry, 2001, pp. 6323-6332, 66(19).
Katritzky, et al., "Syntheses of 3-hydroxymethyl-2-3-dihydrobenzofurans and 3-hydroxymethylbenzofurans", ARKIVOC (Gainesville, FL, United States), 2003, pp. 49-61, vol. 6, CODEN;AGFUAR URL: http://www.arkat-usa.org/ark/journal/2003/Vargoglis/V-622A/6ss.pdf.

(56) References Cited

OTHER PUBLICATIONS

Kawaguchi, et al., "Drug and crystal polymorphism", Journal of Human Environmental Engineering, 2002, pp. 310-317, vol. 4, (in Japanese and partial English translation).
Kaye, et al., "DABCO-catalyzed reactions of salicylaldehydes with acrylate derivatives", Synthetic Communications, 1996, pp. 2085-2097, 26(11).
Kaye, et al., "Does the DABCO-catalyzed reaction of 2-hydroxybenzaldehydes with methyl acrylate follow a Baylis-Hillman pathway?", Organics & Biomolecular Chemistry, 2003, pp. 1133-1138, 1(7).
Keidan, et al., "Effect of BW12C on oxygen affinity of hemoglobin in sickle-cell disease", The Lancet, 1986, pp. 831-834, 327(8485).
Kessar, et al., "An Interesting Application of Photocyclisation in Apophdeadane Alkaloid Synthesis", Tetrahedron Letters, 1987, pp. 5323-5326, 28(44).
Kessar, et al., "Synthesis of Isoindolobenzazepines via photocyclisation of N-(2-formylphenethyl)phthalimide derivatives", Indian Journal of Chemistry, Section B: Organic Chemistry Including Medicinal Chemistry, 1991, pp. 999-1055, 30B(11).
KIRK-Othmer Encyclopedia of Chemical Technology, 2002, pp. 95-147, vol. 8.
Kise, et al., "Electroreductive Intramolecular Coupling of Phthalimides with Aromatic Aldehydes: Application to the Synthesis of Lennoxamine", Journal of Organic Chemistry, 2011, pp. 9856-9880, 76(23).
Klis, et al., "Halogen-lithium exchange versus deprotonation: synthesis of diboronic acids derives from aryl-benzyl ethers", Tetrahedron Letters, 2007, pp. 1169-1173, 48(7).
Li, et al., Database CA Chemical Abstract Service, "Substituted-benzoheterocycle derivatives, preparation, and application for preparation of antiviral or antineoplastic drugs", XP002726578 retrieved from STN Database accession No. 2013:366779 (abstract); RN:1427163-92-5 & CN 102 952 062A, Mar. 6, 2013, 2 pages.
Lin, et al., "Potential Anitumor Agents.8. Derivatives of 3-and 5-Benzyloxy-2-formylpyridine Thiosemicarbazone", Journal of Medicinal Chemistry, 1972, pp. 615-618, 15(6).
Lin, et al., "Synthesis and anticancer activity of benzyloxybenzaldehyde derivatives against HL-60 cells", Bioorganic & Medicinal Chemistry, 2005, pp. 1537-1544, 13(5).
Liu, et al., "Synthesis of Double-Armed Benzo-15-crown-5 and Their Complexation Thermodynamics with Alkali Cations", Journal of Inclusion Phenomena and Macrocyclic Chemistry, 2005, pp. 229-235, 52(3-4).
Luan, et al., "TOPS-MODE model of multiplexing neuroprotective effects of drugs and experimental-theoretic study of new 1,3-rasagiline derivatives potentially useful in neurodegenerative diseases", Bioorganic & Medicinal Chemistry, 2013, pp. 1870-1879, vol. 21.
Mahoney, et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters, 2009, pp. 4706-4709, 50(33).
Majhi, et al., "An efficient synthesis of novel dibenzo-fused ninmembered oxacycles using a sequential Baylis-Hillman reaction and radical cyclization", Synthesis, 2008, pp. 94-100, vol. 1.
Manna, et al., "Synthesis and beta-adrenoreceptor blocking activity of [[3-(alkylamine)-2-hydroxypropyl]oximino] pyridines and 0[3-(alkylamine)-2-hydroxypropyl]methylpyridine ketone oximes derivatives", IL Farmaco, 1996, pp. 679-587, vol. 51, No. 8,9.
Mantyla, et al., "Synthesis, in vitro evaluation, and antileishmanial activity of water-soluble prodrugs of buparvaquone", J. Med. Chem., 2004, pp. 188-195, vol. 47.
Marchetti, et al., "Synthesis and biological evaluation of 5-substituted O4-alkylprimideines as CDK2 inhibitors", Org. Biomol. Chem., 2010, pp. 2397-2407, vol. 8.
Mathur. "Microcrystalline Cellulose" In: "Handbook of Pharmaceutical Excipients, Second Edition", Jan. 1, 1994, The Pharmaceutical Press, London, pp. 84-87.
McKay, et al., "7,11,15,28-Tetrakis[(2-formylphenoxy)methyl]-1,21,23,25-tetramethylresorcin[4]arene cavitand ethyl acetate clathrate at 173 K", Acta Crystallographica, Section E: Structure Reports Online, 2009, pp. 692-693, E65(4), URL: http://journals.lucr.org/e/issues/2009/04/oofl22 33/fl2233.pdf.
McKay, et al., "Microwave-assisted synthesis of a new series of resorcin[4]arene cavitand-capped porphyrin capsules", Organic & Biomolecular Chemistry, 2009, pp. 3958-3968, 7(19).
Merlino, et al., "Development of second generation amidinohydrazones, thio-and semicarbazones as Trypanosoma cruzi-inhibitors bearing benzofuroxan and benzimidazole 1,3-dioxide core scaffolds", MedChemComm, 2010, pp. 216-228, 1(3).
Mesguiche, et al., "4-Alkoxy-2,6-diaminopyrimidine Derivatives: Inhibitors of Cyclin Dependent Kinases 1 and 2", Bioorganic & Medicinal Chemistry Letters, Jan. 2003, pp. 217-222, vol. 13.
Metcalf, et al., "Discovery of GBT440, an Orally Bioavailable R-State Stabilizer of Sickle Cell Hemoglobin," ACS Med. Chem. Lett., 2017, 8, 321-326.
Mitra, et al., "Synthesis and biological evaluation of dibenz[b,f][1,. 5]oxazocine derivatives for agonist activity at x-opioid receptor", European Journal of Medicinal Chemistry, 2011, pp. 1713-1720, 46(5).
Mulwad, et al., "Synthesis and antimicorbial activity of [6'-methyl-4'-methoxy-2-oxo-2H-[1]-benzopyran)-2",4" dihydro-[1", 2", 4"]-triazol-3'-one and 3'phenylthiazolidin-4'-one-phenoxymethyl derivatives of dipyranoquinoline", Pharmaceutical Chemistry Journal, 2011, pp. 427-432. Ahead of Print CODEN: PCJOAU; ISSN: 0091-150.
Muzaffar, et al., "Polymorphism and Drug Availability: a Review", J. of Pharm. (Lahore) 1979, p. 59-66, 1(1).
Nagy, et al., "Selective coupling of methotrexate to peptide hormone carriers through a y-carboxamide linkage of its glutamic acid moiety: Benzotriazol-1-yloxytris(dimethylamino)phosphonium hexafluorophosphate activatiion in salt coupling", Proc. Natl. Acad. Sci., USA, 1993, pp. 6373-6376, vol. 90.
Neelima, et al., "A novel annelation reaction: synthesis of 6H-[1]benzopyrano[4,3-b]quinolines", Chemistry & Industry (London, United Kingdom, 1986, pp. 141-142, vol. 4.
New Introduction of Pharmacology (Sin Yakuzaigaku Soron)(revised 3rd Edition),Apr. 10, 1987, Nankodo Co., Ltd p. 111. (in Japanese with partial English translation).
New Pharmaceutical Preparation (Shin Seizaigaku), Nanzando Co.,Ltd., Apirl 25, 1984, p. 102-103 and pp. 232-233. (in Japanese with partial English translation).
Nnamani, et al., "Pyridyl derivatives of benzaldehyde as potential antisickling agents", Chem. Biodivers., 2008, pp. 1762-1769, 5(9).
Nogrady, Medicinal Chemistry A Biochemical Approach, Oxford University Press, New York, 1985, pp. 388-393.
Nonoyama, et al., "Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron, 1993, pp. 533-543.
Notice of Allowance dated Dec. 19, 2014 for U.S. Appl. No. 13/730,730, 11 pages.
Nozaki, et al., "5.2.2 Bioisosterism", Drug Discovery Chemistry, Dagaku Dojin, 1995, 1st Ed., pp. 98-99, (Japanese with English translation).
Nyerges, et al., "Synthesis of Indazole N-oxides via the 1,7-electrocyclization of azomethine ylides", Tetrahedron Letters, 2001, pp. 5081-5083, 42(30).
Nyerges, et al., "Synthesis of Indazole N-oxides via the 1,7-electrocyclization of azomethine ylides", Tetrahedron Letters, 2004, pp. 9937-9944, 60(44).
OECD SIDS "SIDS Initial Assessment Report for 13th SIAM", Nov. 2001, pp. 1-95.
Office Action dated Aug. 29, 2014, for U.S. Appl. No. 13/730,730, 17 pages.
Office Action dated Dec. 3, 2013, for U.S. Appl. No. 13/730,674, 8 pages.
Office Action dated Jul. 6, 2015, for U.S. Appl. No. 13/815,874, 14 pages.
Office Action dated Jun. 12, 2015, for CN Application No. 201280070743.5, 13 pages.

(56) References Cited

OTHER PUBLICATIONS

Office Action dated Jun. 29, 2015, for U.S. Appl. No. 13/815,810, 19 pages.
Office Action dated Jun. 30, 2014, for U.S. Appl. No. 13/730,674, 9 pages.
Office Action dated Sep. 18, 2013, for U.S. Appl. No. 13/730,674, 10 pages.
Oh, et al., "Solid-phase synthesis of 1,3-oxazolidine derivatives", Tetrahedron Letters, 2000, pp. 5069-5072, vol. 41.
Doshima, Hiroshi, "Crystallization of Polymorphs and Pseudo-polymorphs and its Control", Pharm Stage, 2007, pp. 48-53, 6(10), (in Japanese with partial English translation).
O'Reilly, "Metal-phenoxyalkanoic acid interactions, XXV. The crystal structures of (2-formyl-6-methoxyphenoxy) acetic acid and its zinc(II)complex and the lithium, zinc(II) and cadmium(II) complexes of (2-chlorophenoxy)acetic acied", Australian Journal of Chemistry, 1987, pp. 1146-1159, 40(7)m.
Otsuka, et al., "Effect of Polyorphic Forms of Bulk Powders on Pharmaceutical Properties of Carbamazepine Granules", Chem. Pharm. Bull., 1999, pp. 852-856, 47(6).
Patani, et al., "Bioisosterism: A Rational Approach in Drug Design", J. Chem. Rev., 1996, pp. 3147-3176, 96(8).
Ciganek, "The catalyzed a hydroxyalkylation and a-aminoalkylation of activated olefins (the Morita-Baylis-Hillman reaction", Organic Reactions (Hoboken, NJ, United States), 1997, vol. 51, no page given, CODEN; ORHNBA URL: http://www3.Interscience.wiley.com/cgi-bin/mnwhome/107610747/HOME.
Clinical Trial. Single-Dose PK Study of GBT440 in Subject With Renal Impairment. Mary 19, 2017, https://clinicaltrials.gov/ct2show/NCT03161015. 13 pages.
CMU Pharmaceutical polymorphism, internet, 2002, pp. 1-3, print-out Apr. 3, 2008.
Concise Encyclopedia Chemistry, NY: Walter de Gruyter, 1993, pp. 872-873.
Congreve, et al., "Application of Fragment Screening by X-ray Crystallography to the Discovery of Aminopyridines as Inhibitors of Beta-Secretase", Journal of Medicinal Chemistry, 2007, pp. 1124-1132, vol. 50.
Cos, et al., "Structure-Activity Relationship and Classification of Flavonoids as Inhibitors of Xanthine Oxidase and Superoxide Scavengers", Journal Nat. Prod., 1998, pp. 71-76, vol. 61.
Database Pubchem Compound Dec. 4, 2011 XP 003033770 (11 pages).
Database Registry RN 1184773-12-3, Retrieved from STN, Sep. 15, 2009.
Database Registry, 2011, PN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al., "Detection of polymorphism by powder x-ray diffraction: interfernce by preferred orientation", Am. Pharm. Rev., 2004, pp. 10, 12, 14, 16, 100.
Dean, Analytical Chemistry Handbook. University of Tennese, Knoxville, McGraw-Hill, Inc., 1995, 10.24-10.26.
Deem, "Red Blood Cells and Hemoglobin in Hypoxic Pulmonary Vasoconstriction", Advances in Experimental Medicine and Biology, 2006, pp. 217-231, vol. 588.
Desai, et al., "Preparation of N-[ro-(4-aryl-1-piperazinyl)ethyl/propyl]-3-hydroxyphthalimidines", Indian Journal of Chemistry, 2000, pp. 455-457, vol. 39.
Desideri, et al., "Guanylhydrazones of 3-substituted 2-pyridinecarboxaldehyde and of (2-substituted 3-pyridinyloxy) acet-aldehyde as prostanoid biosynthesis and platelet aggregation inhibitors", European Journal of Medicinal Chemistry, Editions Scientifique Elsevier, Paris, FR, 1991, pp. 455-460, 26(4).
Di Stilo, et al., "New 1, 4-dihydropyridines conjugated to furoxanyl moieties, endowed with both nitric oxide-like and calcium channel antagonist vasodilator activities", Journal of Medicinal Chemistry, 1998, pp. 5393-5401, vol. 41.

Ding, et al., "Crystal structure of bis[μ2-2-(2-formylphenoxy)acetato-O,O]-bis[μ2-2-2-formylphynoxy)acetato-O,O]-octakis(n-buty)tetratin(IV), Sn4O2(C9H7O4)4(C4H9)8", Zeitschrift fuer Kristallographie—New Crystal Structures, 2011, pp. 31-32, 226(1), CODEN:ZKNSFT; ISSN: 1433-7266.
Doelker, English translation of Ann. Pharm. FR., 2002, pp. 161-176, vol. 60.
Doelker, English translation of S.T.P., Pratiques, 1999, pp. 399-409, 9(5).
Einfalt, et al., "Methods of amorphization and investigation of the amorphous state", Acta Pharm, 2013, pp. 305-334, vol. 63.
Elwahy, " Synthesis of new benzo-substituted macrocyclic containing quinoxaline subunits", Tetrahedron, 2000, pp. 897-907, 56(6) CODEN; TETRAB; ISSN:0040-4020.
Epsztajn, et al., "Application of organolithium", Tetrahedron, Elsevier Science Publishers, Amsterdam, NL, 1991, pp. 1697-1706, 47(9).
European Application No. 17796828.6, filed May 11, 2017, Search Report and Written Opinion, dated Nov. 11, 2019, 7 pages.
European Search Report and Search Opinion dated Aug. 4, 2015, for EP Application No. 12862525.8, 9 pages.
European Search Report and Search Opinion dated Jul. 21, 2016, for EP Application No. 14769616.5, 8 pages.
European Search Report and Search Opinion dated May 28, 2015, for EP Application No. 12862096.0, 13 pages.
European Search Report and Search Opinion dated Nov. 16, 2016, for EP Application No. 16194019.2, 13 pages.
European Search Report and Search Opinion dated Sep. 26, 2016, for EP Application No. 14768759.4, 6 pages.
Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).
Extended European Search Report and Search Opinion dated Jul. 18, 2016, for EP Application No. 14770695.6, 13 pages.
Extended European Search Report and Search Opinion dated Jul. 20, 2016, for EP Application No. 14768414.6, 10 pages.
Extended European Search Report and Search Opinion dated Jul. 7, 2016, for EP Application No. 14768317.1, 7 pages.
Extended European Search Report and Search Opinion dated May 17, 2017, for EP Application No. 15746995.8, 8 pages.
Extended European Search Report and Search Opinion dated Nov. 11, 2019, for EP Application No. 17796828.6, 7 pages.
Extended European Search Report and Search Opinion dated Nov. 23, 2015, for EP Application No. 12862525.8, 16 pages.
Extended European Search Report and Search Opinion, dated Sep. 22, 2020 for EP Application No. 20167746.5, 8 pages.
FDA approves voxelotro for sickle cell disease, Dated Nov. 25, 2019. https://www.fda.gov/drugs/resources-information-approved-drugs/fda-approves-voxelotor-sickle-cell-disease, 2 pages.
Gadaginamath, et al., "Synthesis and antibacterial activity of novel 1-butyl-2-phenoxyl2-phenylthlol2-aminomethyl-5-methoxyindole derivatives", Polish Journal of Chemistry, 1997, pp. 923-928, 71(7), CODEN: PJCHDQ; ISSN: 0137-5083.
Gao, et al., "A novel one-pot three-step synthesis of 2-(1-benzofuran-2-yl)quinoline-3-carboxylic acid derivatives", Journal of the Brazilian Chemical Society, 2010, pp. 806-812, 21(5). CODEN; JOCSET; ISSN: 0103-5053.
GBT Announces Positive Top-line Data from Part A of the Phase 3 HOPE Study of Voxelotor in Sickle Cell Disease, Press Release dated Jun. 27, 2018. Available at http://ir.gbt.com/phoenix.zhtml?c=254105&p=irol-newsArticle&ID=2356168.
Ghate, et al., "Synthesis of vanillin ethers from 4-(bromomethyl) coumarins as anti-inflammatory agents", European Journal Medicinal Chemistry, 2003, pp. 297-302, 38(3), CODEN; EJMCA5; ISSN: 0223-5234.
Gibson, et al., "Novel small molecule bradykinin B2 receptor antagonists", Journal of Medicinal Chemistry, 2009, pp. 4370-4379, vol. 52.
Glasson, et al., "Metal Template Synthesis of a Tripodal Tris(bipyridyl) Receptor that Encapsulates a Proton and an Iron (ii) Centre in a Pseudo Cage", Aust. J. Chem., 2012, pp. 1371-1376, vol. 65.
Goodman and Gilman's, The Pharmacological Basis of Therapeutics, 10th edition, 2001, Chpater 1, pp. 3-29.

(56) References Cited

OTHER PUBLICATIONS

Grashey, "The nito group as a 1,3-dipole in cycloadditions", Angewandte Chemie, 1962, pp. 155, vol. 74. CODEN; ANCEAD; ISSN: 0044-8249.
Green, et al., Protective Groups in Organic Synthesis, Third Edition, 1999, pp. 260-261.
Gu, et al., "Grouping solvents by statistical analysis of solvent property parameters: implication to polymorph screening", Int J Pharm. Sep. 28, 2004;283(1-2):117-25.
Guillaumel, et al., "Synthetic routes to 2-(2-benzofuranyl)benzoic acids and their cyclization into benz[6]indeno[2,1-d]furan-10-ones", Journal of Heterocyclic Chemistry, 1990, pp. 1047-1051, vol. 27. doi:10.1002/jhet.5570270444.
Guillory, (in Britain ed.) "Polymorphism in Pharmaceutical Solids", NY, Marcel Dekker, Inc., 1999, pp. 183-226, vol. 1-2.
Gunter, et al., "Structural control of co-receptor binding in porphyrin-bipyridinium supramoledcular assemblies", Journal of the Chemical Society, Perkin Transactions 1: Organic and Bio-Organic Chemistry (1998), pp. 1945-1958, vol. 12, CODEN: JCPRB4; ISSN: 0300-922X.
Paul, et al., "Hydroxyl directed C-arylation: synthesis of 3-hydroxyflavones and 2-phenyl-3-hydroxy pyran-4-ones under transition-metal free conditions", Org. Biomol. Chem., 2018, 16:444-451.
Pearson, Emma L., et al., "Experimental and Computational Studies into an ATPH-Promoted exo-Selective IMDS Reaction: A Short Total Synthesis of Δ9—THC**", Chemistry A European Journal, 2010, pp. 8280-8284, 16(28).
Perez, et al., "Preparation of new 1,2-disubstituted ferrocenyl ammonium salt", Polyhedron, 2009, pp. 3115-3199, 28(14).
Perkins, et al., "Manganese(II), Iron(II), cobalt(II), and cooper(II) complexes of an extended inherently chiral tris-bipyridyl cages", Proceedings of the National Academy of Sciences, USA, 2006, pp. 532-537, 103(3).
Pharmaceutical Affairs Bureau Notification, Ministry of Health, Labour and Welfare, 21001, 46 pages, (in Japanese with partial English translation).
Pharmacy-Foundation and Application-(Chozaigaku, Kiso to Ouyou), Nanzando Co.,Ltd., Sep. 20, 1977 p. 142-145. (in Japanese with partial English translation).
Potapov, et al., "A convenient synthesis of heterocyclic compounds containing 11-oxo-6, 11, 12, 13-tetrahydrodibenzo[b,g][1,5]oxazonine fragment", Mendeleev Communications, 2009, pp. 287-289, vol. 19.
Prohens, et al., "Polymorphism is pharmaceutical industry", The Pharmacist, Apr. 1, 2007, pp. 58-68, vol. 373. (in Spanish with English abstract).
Pubchem CID 54009805 Create Date: Dec. 4, 2011, p. 1.
Pubchme CID 54883281 Create Date: Aug. 19, 2012, p. 1.
Reagan-Shaw, et al., "Dose translation from animal to human studies revisited", The FASEB Journal. Mar. 2007; pp. 659-661, vol. 22.
Remington's Pharmaceutical Sciences, 17th Edition, A. Gennaro editor, Easton Pennsylvania. Table of Contents, 1985.
Rigby, et al., "Total Synthesis of (+)-Narciclasine", Journal of American Chemical Society, 1997, pp. 12655-1256, vol. 119.
Rodriguez-Spong, et al., "General principles of pharmaceutical solid polymorphism: a supramolecular perspective", Advance Drug Delivery Review, Feb. 23, 2004, pp. 241-274, 56(3).
Rolan, et al., "The pharmacokinetics, tolerability and pharmacodynamics of tucaresol (589C80); 4[2-formyl-3-hyddroxyphenoxymethyl]benzoic acid), a potential anti-sickling agent, following oral administration to healthy subjects", British Journal of Clinical Pharmacology, 1993, pp. 419-425, 35(4).
Rooseboom, et al., "Enzyme-catalyzed activation of anticancer prodrugs", Pharmacol Rev., 2004, pp. 53-102, vol. 56.
Ruchirawat, et al., "A novel synthesis of aporhoeadanes", Tetrahedron Letters, 1984, pp. 3485-3488, 25(32).

Safo, et al., "Structural basis for the potent antisickling effect of a novel class of five-membered heterocyclic aldehydic compounds", J. Med. Chem., Sep. 9, 2004, pp. 4665-4676, 47(19).
Sahakitpichan, et al., "A practical and highly efficient synthesis of lennoxamine and related isoindoloenzazepines", Tetrahedron, 2004, pp. 4169-4172, 60(19).
Sahm, et al., "Synthesis of 2-arylbenzofurans", Justus Liebigs Annalen der Chemie, 1974, pp. 523-538, vol. 4.
Sainsbury, et al., "1,2-Dihydroisoquinolines, IV, Acylation", Tetrahedron, 1966, pp. 2445-2452, 22(8).
Sarodnick, et al., "Quinoxalines XV, Convenient Synthesis and Structural Study of Pyrazolo[1,5-a]quinoxalines", Journal of Organic Chemistry, 2009, pp. 1282-1287, 74(3).
Schudel, et al., "Über die Chemie des Vitamins E", Helvetica Chimica Acta, 1963, pp. 636-649, vol. 66.
Seddon, "Pseudopolymorph: A Polemic", The QUILL Centre, The Queen's University of Belfast, United Kingdom, Jul. 26, 2004, 2 pages.
Shetty, et al., "Palladium catalyzed alpha-arylation of methyl isobutyrate and isobutyronitrile: an efficent synthesis of 2,5-disubstituted benzyl alcohol and amine intermediates", Tetrahedron Letters, 2006, pp. 8021-8024, vol. 47.
Shin, et al. "Interpretation of Animal Dose and Human Equivalent Dose for Drug Development", The Journal of Korean Oriental Medicine. 2010; 31(3):1-7.
Siddiqui, et al., "The Presence of Substitutents on the Aryl Moiety of the Aryl Phosphoramidate Derivative of d4T Enhances Anti-HIV Efficacy in Cell Culture-Activity Relationship", Journal of Medicinal Chemistry, 1999, pp. 393-399, vol. 42.
Silva, et al., "Advances in prodrug design", Mini Rev. Med. Chem., 2005, pp. 893-914, 5(10).
Singh, et al., "Reductive-Cyclization-Mediated Synthesis of Fused Polycyclic Quinolines from Baylis-Hillman Adducts of Acrylonitrile: Scope and Limitations", European Journal of Organic Chemistry, 2009, pp. 3454-3466, vol. 20.
Singhal, et al., "Drug Polymorhism and Dosage Form Design: a Practical Perspective", Advanced Drug Delivery Reviews, 2004, pp. 335-347, vol. 56.
Sobolev, et al., "Effect of acyl chain length and branching on the enantioselectivity of Candida rugosa lipase in the kinetic resolution of 4-(2-difluoromethoxyphenyl)-substituted 1,4-dihydropyridine 3,5-diesters", Journal of Organic Chemistry, 2002, pp. 401-410, vol. 67.
Srivastava, et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry, 1989, pp. 562-573, 23B(7).
Starke, et al., "Quinoxalines, Part 13: Synthesis and mass spectrometric study of aryloxymethylquinoxalines and benzo[b]furylquinoxalines", Tetrahedron, 2004, pp. 6063-6078, 60(29).
Stetinova, et al., "Synthesis and Properties of 4-Alkylaminomethyl and 4-Alkoxymethyl Derivatives of 5-Methyl-2-Furancarboxylic Acid", Collection Czechosloval Chem. Commun., 1985, pp. 2186-2192, vol. 51.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley, "Solubilizing excipients in oral and injectable formulations", Pharm Res., Feb. 2004, pp. 201-230, 21(2).
Swann, et al., "Rates of reductive elimination of substituted nitrophenols from the (indol-3-yl)methyl position of indolequinones", Journal of Chemical Society, Perkin Transaction2, 2011, pp. 1340-1345, vol. 8.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride", J. of Pharm. Sci., 2003. pp. 831-838, 92(4).
Takata, Noriyuki, "API form screening and selection in drug discovery stage", Pharm Stage, 2007, pp. 20-25, 6(10), (in Japanese with partial English translation).
Testa, et al., "Hydrolysis in Drug and Prodrug Metabolism", Jun. 2003, Wiley-VCH, Zurich, pp. 419-534.

(56) References Cited

OTHER PUBLICATIONS

The Pharmacopoeia of Japan the Sixteen edition, 2011 pp. 64-68 2.58 X-ray powder diffraction measuring method p. 2070 (in Japanese with partial English translation).

Tome, et al., "Product class 13: 1,2,3-triazoles", Science of Synthesis, 2004, pp. 415-601, vol. 13.

Tsuge, et al., "Suppressive Effect of Vitamin B6-Sugar Derivatives on The Proliferation of Feline Mammary Tumor Cell", FRM. Vitamins (Japan), 2006; 80(11):537-542. (In Japanese with English Abstract).

Van Halbeek, H., et al. "Sialic Acid in Permethylation Analysis: Prepared and Identification of Partially O-Methylated Derivatives of Methyl N-Acetyl-N-Methyl-beta-D-Neuraminate Methyl Glycoside", Carbohydrate Research, Jan. 1, 1978, pp. 51-62, 60(1).

VanRompaey, et al., "A versatile synthesis of 2-substituted 4-amino-1,2,4,5-tetrahydro-2-benzazepine-3-ones", Tetrahedron, 2003, pp. 4421-4432, 59(24).

VanRompaey, et al., "Synthesis and evaluation of the 3B2-turn properties of 4-amino-1,2,4,5-tetrahydro-2-benzazepin-3-ones and of their spirocyclic derivative", European Journal of Organic Chemistry, 2006, pp. 2899-2911, vol. 13.

Vicente, et al., "Carbopalladation of Maleate and Fumarate Esters and 1, 1-Dimethylallene with Ortho-Substituted Aryl Palladium Complexes", Organometallics, 2010, pp. 409-416, 29(2).

Vichinsky, "Emerging "A" therapies in hemoglobinopathies: agonist, antagonists, antioxidants, and arginine", Hematology, 2012, pp. 271-275.

Kratochvil, Chapter 8 Solid Forms of Pharmaceutical Molecules, J. Sestak, et al., (eds.), Glassy, Amorphous and Nano-Crystalline Materials. Hot Topics in Thermal Analysis and Calorimetry, 2011, pp. 129-140, vol. 8.

Kraus, et al., "Michael additions in anhydrous media. A novel Synthesis of oxygeriated coumarins", J. Org. Chem., 1979, pp. 2480-2482, 44(14).

Krow, "The Baeyer-Villiger oxidation of ketones and aldehydes", Organic Reactions (Hoboken, NJ, United States). 1993, 43, No pages given, CODEN; ORHNBA URL: http://www.3.interscience.wiley.com/cgi-bin/mrwhome/107610747/HOME.

Kucera, et al.; "Evaluation of Ceolus(TM) microcrystalline cellulose grades for the direct compression of enteric-coated pellets", Drug Development and Industrial Pharmacy. Mar. 1, 2012; 38(3):341-350.

Lakkannavar, et al., "4-[2'-benzylideneantino aryloxymethyl] coumarins E and Z isomers", Indian Jouranl of Heterocyclic Chemistry 1995, pp. 303-304, 4(4).

Lehrer, et al. "GBT440, a novel ana polymerization agent, for the treatment of sickle cell disease", Global Blood Therapeutics. Apr. 1, 2016. (50 pages) Retrieved from the Internet: http://casicklecell.org/img/PresentationSlidesWebinar3.pdf.

Li, et al., "Iron-Catalyzed Cascase Arene-Aldehyde/Cyclizations for the Highly Efficient Synthesis of Xanthenes and Its Analogous: Observation of a C-C Bond Cleavage in Indole-Based Triarylmethanes". Journal of Organic Chemistry, 2009, pp. 6797-6801, vol. 74.

DOSING REGIMENS FOR 2-HYDROXY-6-((2-(1-ISOPROPYL-1H-PYRAZOL-5-YL)PYRIDIN-3-YL)METHOXY)BENZALDEHYDE

1. CROSS-REFERENCE TO RELATED APPLICATIONS

The present application is a continuation of U.S. application Ser. No. 17/559,156, filed Dec. 22, 2021, which is a continuation of U.S. application Ser. No. 17/326,045, filed May 20, 2021, which is a continuation of U.S. application Ser. No. 15/368,142, filed Dec. 2, 2016, now U.S. Pat. No. 11,020,382, which claims the benefit of priority of U.S. Provisional Application No. 62/263,554, filed Dec. 4, 2015, and U.S. Provisional Application No. 62/375,832, filed Aug. 16, 2016, the content of each of which is hereby incorporated by reference in its entirety.

2. FIELD OF THE INVENTION

Provided herein are compounds, compositions, formulations, dosage forms and methods for the treatment of sickle cell disease. As provided herein, such treatment may comprise administering to a subject, or preparing for administration to such subject, 2-hydroxy-6-((2-(1-isopropyl-1H-pyrazol-5-yl)pyridin-3-yl)-methoxy)benzaldehyde, or a polymorph thereof, in certain dosing regimens. Also provided herein is a capsule dosage form comprising high drug loads of 2-hydroxy-6-((2-(1-isopropyl-1H-pyrazol-5-yl)pyridin-3-yl)methoxy)benzaldehyde or a polymorph thereof.

3. BACKGROUND OF THE INVENTION

Hemoglobin (Hb) is a tetrameric protein in red blood cells that transports up to four oxygen molecules from the lungs to various tissues and organs throughout the body.

Hemoglobin binds and releases oxygen through conformational changes, and is in the tense (T) state when it is unbound to oxygen and in the relaxed (R) state when it is bound to oxygen. The equilibrium between the two conformational states is under allosteric regulation. Natural compounds such as 2,3-bisphosphoglycerate (2,3-BPG), protons, and carbon dioxide stabilize hemoglobin in its de-oxygenated T state, while oxygen stabilizes hemoglobin in its oxygenated R state. Other relaxed R states have also been found, however their role in allosteric regulation has not been fully elucidated.

Sickle cell disease is a prevalent disease particularly among those of African and Mediterranean descent. Sickle hemoglobin (HbS) contains a point mutation where glutamic acid is replaced with valine, allowing the T state to become susceptible to polymerization to give the HbS containing red blood cells their characteristic sickle shape. The sickled cells are also more rigid than normal red blood cells, and their lack of flexibility can lead to blockage of blood vessels. Certain synthetic aldehydes have been found to shift the equilibrium from the polymer forming T state to the non-polymer forming R state (Nnamani et al., Chemistry & Biodiversity Vol. 5, 2008 pp. 1762-1769) by acting as allosteric modulators to stabilize the R state through formation of a Schiff base with an amino group on hemoglobin.

U.S. Pat. No. 7,160,910 discloses 2-furfuraldehydes and related compounds that are also allosteric modulators of hemoglobin. One particular compound, 5-hydroxymethyl-2-furfuraldehyde (5HMF), was found to be a potent hemoglobin modulator both in vitro and in vivo. 5HMF is currently in clinical trials for treatment of sickle cell disease. However, 5HMF requires 4 times daily dosing of 1,000 mg (see, e.g., ClinicalTrials.gov; NCT01987908). This requirement for frequent dosing at relatively high amounts can present problems with patient compliance and high treatment costs.

Accordingly, there exists a need for effective methods of treating sickle cell disease, which use compounds that are effective when administered at lower doses.

4. SUMMARY

Applicant has unexpectedly found that Compound 1 disclosed herein is therapeutically effective in the treatment of sickle cell disease (SCD) at low doses, in spite of the large concentration of hemoglobin in red cells (5 nM in red cells).

In one aspect, provided herein are methods for treating sickle cell disease in a patient comprising administering to the patient Compound 1:

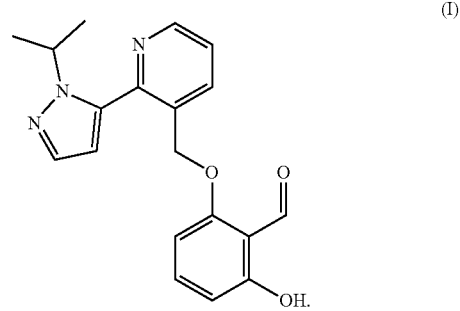 [SMILES: CC(C)n1nccc1-c1ncccc1COc1cccc(O)c1C=O]

(I)

wherein the compound is administered in a dose of from about 500 mg/day to about 1500 mg/day. In one embodiment of the first aspect, Compound 1 is administered in a dose of about 1100, about 1200, about 1300, about 1400, or about 1500 mg/day. In another embodiment of the first aspect, Compound 1 is administered in a dose of about 1050, about 1100, about 1150, about 1200, about 1250, about 1300, about 1350, about 1400, about 1450, or about 1500 mg/day. In another embodiment of the first aspect, the compound is administered in a dose of about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg/day. In another embodiment of the first aspect, the compound is administered in a dose of from about 500 mg/day to about 1000 mg/day. In another embodiment of the first aspect, the compound is administered in a dose of about 500, about 550, about 600, about 650, about 700, about 750, about 800, about 850, about 900, about 950, or about 1000 mg/day. In another embodiment of the first aspect, the compound is administered in a dose of about 600, about 650, about 700, about 750, about 800, about 850, or about 900 mg/day. In yet another embodiment of the first aspect, the compound is administered in a dose of from about 500 mg/day to about 900 mg/day. In yet another embodiment of the first aspect, the compound is administered in a dose of from about 600 mg/day to about 900 mg/day. In yet another embodiment of the first aspect the compound is administered in a dose of about 700 mg/day. In yet another embodiment of the first aspect, the compound is administered in a dose of about 600 mg/day. In yet another embodiment of the first aspect, the compound is administered in a dose of about 900 mg/day. In yet another embodiment of the first aspect, the compound is administered in a dose of about 1200 mg/day. In yet another embodiment of the first aspect, the compound is administered in a dose of about 1500 mg/day. In yet another embodiment of the first aspect, the compound is administered in a dose of 900 mg/day. In yet another embodiment of the first aspect, the compound is administered in a dose of 1200 mg/day. In yet another embodiment of the first aspect, the compound is administered in a dose of 1500 mg/day. In yet another embodiment of the first aspect and embodiments contained therein, the patient is in need to treatment.

In a second embodiment of the first aspect and embodiments contained therein above, the compound is administered once daily.

In a third embodiment of the first aspect and embodiments contained therein above (which include the second embodiment), the dose is administered in a capsule or tablet. Within the third embodiment, in one subembodiment, the dose is administered in a 100 mg or a 300 mg capsule. Within the third embodiment, in another subembodiment, the dose is administered in a 300 mg capsule.

In a fourth embodiment of the first aspect and embodiments contained therein above (including the second and third embodiments and subembodiments contained therein), Compound 1 is a crystalline ansolvate form. In one embodiment, the crystalline ansolvate is Form II characterized by at least one X-ray powder diffraction peak (Cu Kα radiation) selected from 13.37°, 14.37°, 19.95° and 23.92° 2θ (each ±0.2° 2θ). In one embodiment, the crystalline ansolvate is characterized by at least one X-ray powder diffraction peak (Cu Kα radiation) selected from 13.37°, 14.37°, 19.95° and 23.92° 2θ (each ±0.2° 2θ). In another embodiment, Form II is characterized by at least two X-ray powder diffraction peaks (Cu Kα radiation) selected from 13.37°, 14.37°, 19.95° and 23.92° 2θ (each ±0.2° 2θ). In another embodiment, the crystalline ansolvate is characterized by at least two X-ray powder diffraction peaks (Cu Kα radiation) selected from 13.37°, 14.37°, 19.95° and 23.92° 2θ (each ±0.2° 2θ). In yet another embodiment, Form II is characterized by at least three X-ray powder diffraction peaks (Cu Kα radiation) selected from 13.37°, 14.37°, 19.95° and 23.92° 2θ (each ±0.2° 2θ). In yet another embodiment, the crystalline ansolvate is characterized by at least three X-ray powder diffraction peaks (Cu Kα radiation) selected from 13.37°, 14.37°, 19.95° and 23.92° 2θ (each ±0.2° 2θ). In yet another embodiment, Form II is characterized by X-ray powder diffraction peaks (Cu Kα radiation) of 13.37°, 14.37°, 19.95° and 23.92° 2θ (each ±0.2° 2θ). In yet another embodiment, the crystalline ansolvate is characterized by X-ray powder diffraction peaks (Cu Kα radiation) of 13.37°, 14.37°, 19.95° and 23.92° 2θ (each ±0.2° 2θ). In yet another embodiment, Form II is characterized by an X-ray powder diffraction pattern (Cu Kα radiation) substantially similar to that of FIG. 1. In yet another embodiment, the crystalline ansolvate is characterized by an X-ray powder diffraction pattern (Cu Kα radiation) substantially similar to that of FIG. 1. In yet another embodiment, the crystalline ansolvate form of Compound 1 is substantially free of Form I and/or Form N. Form I of Compound 1 is characterized by at least three X-ray powder diffraction peaks (Cu Kα radiation) at 12.82°, 15.74°, 16.03°, 16.63°, 17.60°, 25.14°, 25.82° and 26.44° 2θ (each ±0.2° 2θ); and Form N of Compound 1 is characterized by at least three X-ray powder diffraction peaks (Cu Kα radiation) at 11.65°, 11.85°, 12.08°, 16.70°, 19.65° and 23.48° 2θ (each ±0.2° 2θ).

In a second aspect, provided is a method of treating interstitial pulmonary fibrosis in a patient comprising administering to the patient about 1100 mg/day to about 1500 mg/day of Compound 1 optionally in combination with an anti-fibrotic agent. In one embodiment, the anti-fibrotic agent is selected from pirfenidone, nintenabib, and systemic corticosteroids.

In one embodiment of the second aspect, Compound 1 is administered in a dose of about 1100, about 1200, about 1300, about 1400, or about 1500 mg/day. In another embodiment of the second aspect, Compound 1 is administered in a dose of about 1050, about 1100, about 1150, about 1200, about 1250, about 1300, about 1350, about 1400, about 1450, or about 1500 mg/day. In another embodiment of the second aspect, the compound is administered in a dose of about 1200 mg/day. In another embodiment of the second aspect, the compound is administered in a dose of about 1500 mg/day. In another embodiment of the second aspect, the compound is administered in a dose of 1200 mg/day. In another embodiment of the second aspect, the compound is administered in a dose of 1500 mg/day. In yet another embodiment of the second aspect and embodiments contained therein, the patient is in need to treatment.

In a second embodiment of the second aspect and embodiments contained therein above, the compound is administered once daily.

In a third embodiment of the second aspect and embodiments contained therein above (which include the second embodiment), the compound is administered in a capsule or tablet. Within the third embodiment, in one subembodiment, the compound is administered in a 100 mg or a 300 mg capsule. Within the third embodiment, in another subembodiment, the compound is administered in a 300 mg capsule.

In a fourth embodiment of the second aspect and embodiments contained therein above (including the second and third embodiments and subembodiments contained therein), Compound 1 is a crystalline ansolvate form. In one embodiment, the crystalline ansolvate is Form II characterized by at least one X-ray powder diffraction peak (Cu Kα radiation) selected from 13.37°, 14.37°, 19.95° and 23.92° 2θ (each ±0.2° 2θ). In one embodiment, the crystalline ansolvate is characterized by at least one X-ray powder diffraction peak (Cu Kα radiation) selected from 13.37°, 14.37°, 19.95° and 23.92° 2θ (each ±0.2° 2θ). In another embodiment, Form II is characterized by at least two X-ray powder diffraction peaks (Cu Kα radiation) selected from 13.37°, 14.37°, 19.95° and 23.92° 2θ (each ±0.2° 2θ). In another embodiment, the crystalline ansolvate is characterized by at least two X-ray powder diffraction peaks (Cu Kα radiation) selected from 13.37°, 14.37°, 19.95° and 23.92° 2θ (each ±0.2° 2θ). In yet another embodiment, Form II is characterized by at least three X-ray powder diffraction peaks (Cu Kα radiation) selected from 13.37°, 14.37°, 19.95° and 23.92° 2θ (each ±0.2° 2θ). In yet another embodiment, the crystalline ansolvate is characterized by at least three X-ray powder diffraction peaks (Cu Kα radiation) selected from 13.37°, 14.37°, 19.95° and 23.92° 2θ (each ±0.2° 2θ). In yet another embodiment, Form II is characterized by X-ray powder diffraction peaks (Cu Kα radiation) of 13.37°, 14.37°, 19.95° and 23.92° 2θ (each ±0.2° 2θ). In yet another embodiment, the crystalline ansolvate is characterized by X-ray powder diffraction peaks (Cu Kα radiation) of 13.37°, 14.37°, 19.95° and 23.92° 2θ (each ±0.2° 2θ). In yet another, Form II is characterized by an X-ray powder diffraction pattern (Cu Kα radiation) substantially similar to that of FIG. 1. In yet another, the crystalline ansolvate is characterized by an X-ray powder diffraction pattern (Cu Kα radiation) substantially similar to that of FIG. 1.

In a third aspect, provided is a capsule dosage form comprising:
  (i) from about 65% to about 93% w/w of Compound 1 or a polymorph thereof; and
  (ii) from about 2% to about 10% w/w a binder;
wherein w/w is relative to the total weight of the formulation (excluding the weight of the capsule). With regards to the capsule formulation; "about" means±10% of a given range or value.

In one embodiment of the third aspect, the capsule dosage form further comprises from about 2% to about 10% a disintegrant.

In a second embodiment of the third aspect, the capsule dosage form further comprises from about 2% to about 10% a disintegrant and about 2% to 35% a filler.

In a fourth aspect, provided is a capsule dosage form comprising:
  (i) from about 65% to about 86% w/w of Compound 1 or a polymorph thereof;
  (ii) from about 2% to about 6% w/w a binder;
  (iii) from about 6% to about 25% w/w a filler;
  (iv) from about 2% to 6% w/w a disintegrant; and
  (iv) from about 0.5% to about 1.5% w/w a lubricant;
wherein w/w is relative to the total weight of the formulation (excluding the weight of the capsule). With regards to the capsule formulation; "about" means±10% of a given range or value.

In one embodiment of the fourth aspect, the capsule dosage form comprises:
  (i) from about 65% to about 86% w/w of Compound 1 or a polymorph thereof;
  (ii) from about 2% to about 6% w/w a binder;
  (iii) from about 3.5% to about 25% w/w an insoluble filler or 2.5% to 25% w/w of soluble filler or 2.5% to 25% of a combination of soluble or insoluble filler;
  (iv) from about 2% to 6% w/w a disintegrant; and
  (iv) from about 0.5% to about 1.5% w/w a lubricant.

In a second embodiment of the fourth aspect, the capsule dosage form comprises:
  (i) about 86% w/w of Compound 1 or a polymorph thereof;
  (ii) about 4% w/w a binder;
  (iii) about 3.5% w/w an insoluble filler and 2.5% w/w of soluble filler;
  (iv) about 3.5% w/w a disintegrant; and
  (iv) about 0.5% w/w a lubricant.

In a third embodiment of the fourth aspect, the capsule dosage form comprises:
  (i) 85.71% w/w of Compound 1 or a polymorph thereof;
  (ii) 4% w/w a binder;
  (iii) 3.64% w/w an insoluble filler and 2.65% w/w of soluble filler;
  (iv) 2.65% w/w a disintegrant; and
  (iv) 0.5% w/w a lubricant.

In one embodiment of the third and fourth aspects, and embodiments contained therein:
  Compound 1 is Form II substantially free of Form I and/or N;
  the binder is hypromellose;
  the insoluble filler is microcrystalline cellulose
  the soluble filler is lactose monohydrate;
  the disintegrant is croscarmellose sodium; and
  the lubricant is magnesium stearate.

In another embodiment of the third and fourth aspects, and embodiments contained therein, the capsule contains 300 mg of Compound 1 Form II substantially free of Form I and/or N.

In another embodiment of the third and fourth aspects, and embodiments contained therein, Compound 1 is a crystalline ansolvate form. In one embodiment, the crystalline ansolvate is Form II characterized by at least one X-ray powder diffraction peak (Cu Kα radiation) selected from 13.37°, 14.37°, 19.95° and 23.92° 2θ (each ±0.2° 2θ). In one embodiment, the crystalline ansolvate is characterized by at least one X-ray powder diffraction peak (Cu Kα radiation) selected from 13.37°, 14.37°, 19.95° and 23.92° 2θ (each ±0.2° 2θ). In another embodiment, Form II is characterized by at least two X-ray powder diffraction peaks (Cu Kα radiation) selected from 13.37°, 14.37°, 19.95° and 23.92° 2θ (each ±0.2° 2θ). In another embodiment, the crystalline ansolvate is characterized by at least two X-ray powder diffraction peaks (Cu Kα radiation) selected from 13.37°, 14.37°, 19.95° and 23.92° 2θ (each ±0.2° 2θ). In yet another embodiment, Form II is characterized by at least three X-ray powder diffraction peaks (Cu Kα radiation) selected from 13.37°, 14.37°, 19.95° and 23.92° 2θ (each ±0.2° 2θ). In yet another embodiment, the crystalline ansolvate is characterized by at least three X-ray powder diffraction peaks (Cu Kα radiation) selected from 13.37°, 14.37°, 19.95° and 23.92° 2θ (each ±0.2° 2θ). In yet another embodiment, Form II is characterized by X-ray powder diffraction peaks (Cu Kα radiation) of 13.37°, 14.37°, 19.95° and 23.92° 2θ (each ±0.2° 2θ). In yet another embodiment, the crystalline ansolvate is characterized by X-ray powder diffraction peaks (Cu Kα radiation) of 13.37°, 14.37°, 19.95° and 23.92° 2θ (each ±0.2° 2θ). In yet another, Form II is characterized by an X-ray powder diffraction pattern (Cu Kα radiation) substantially similar to that of FIG. 1. In yet another, the crystalline ansolvate is characterized by an X-ray powder diffraction pattern (Cu Kα radiation) substantially similar to that of FIG. 1.

In another embodiment of the third and fourth aspects, and embodiments contained therein, the capsule contains 300 mg±5% of Compound 1, wherein compound 1 is a crystalline ansolvate form that is characterized by at least two X-ray powder diffraction peaks (Cu Kα radiation) selected from 13.37°, 14.37°, 19.95° and 23.92° 2θ (each ±0.2° 2θ); wherein the crystalline ansolvate form is substantially free of Form I and/or N; wherein Form I is characterized by at least three X-ray powder diffraction peaks (Cu Kα radiation) selected from 12.82°, 15.74°, 16.03°, 16.63°, 17.60°, 25.14°, 25.82° and 26.44° 2θ (each ±0.2° 2θ); and wherein Form N is characterized by at least three X-ray powder diffraction peaks (Cu Kα radiation) selected from 11.65°, 11.85°, 12.08°, 16.70°, 19.65° and 23.48° 2θ (each ±0.2° 2θ).

Due to the high drug loading, higher doses of Compound 1 can be delivered with minimal number of dosing units making it practical from a convenience, compliance and marketing perspective. Additionally, in spite of high drug loading, the capsule formulation displays superior physical properties due to the appropriate ratio of the binder to the wet granulation process parameters. Further, the combination of soluble and insoluble fillers gives granule strength, flow properties and disintegration that provides the desired therapeutic effect.

5. BRIEF DESCRIPTION OF THE FIGURES

Figure 7A:
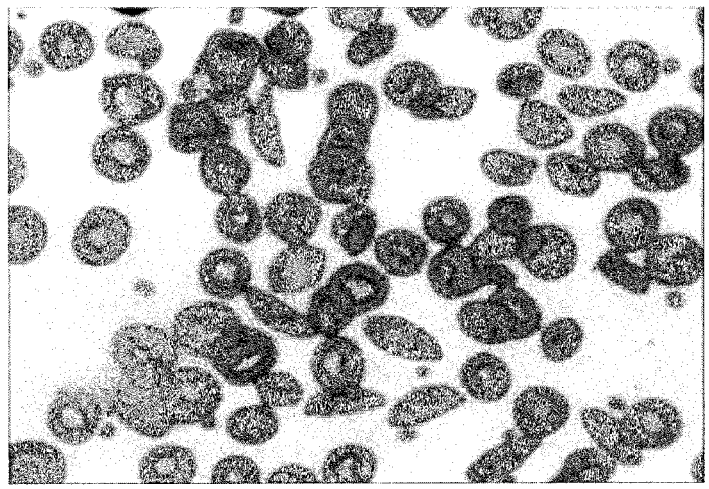
Figure 7B:
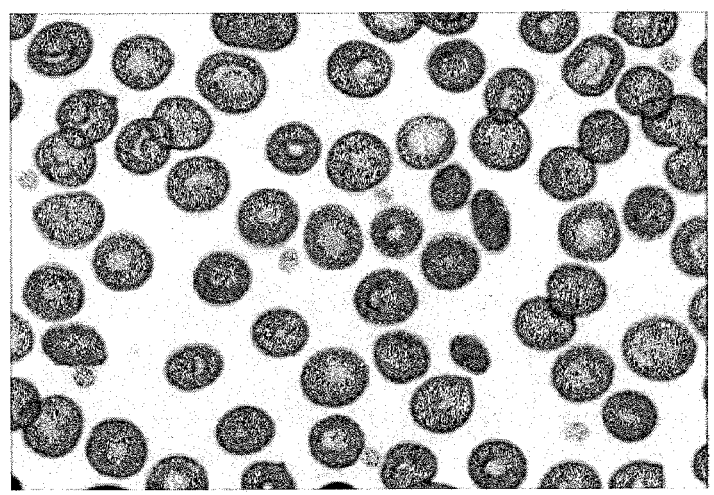

FIGS. 7A-7B provide representative images of sickle cells from subject treated with 700 mg of Compound 1, over a period of one day as shown in FIG. 7A; and twenty-eight (28) days as shown in FIG. 7B.

Figure 8:
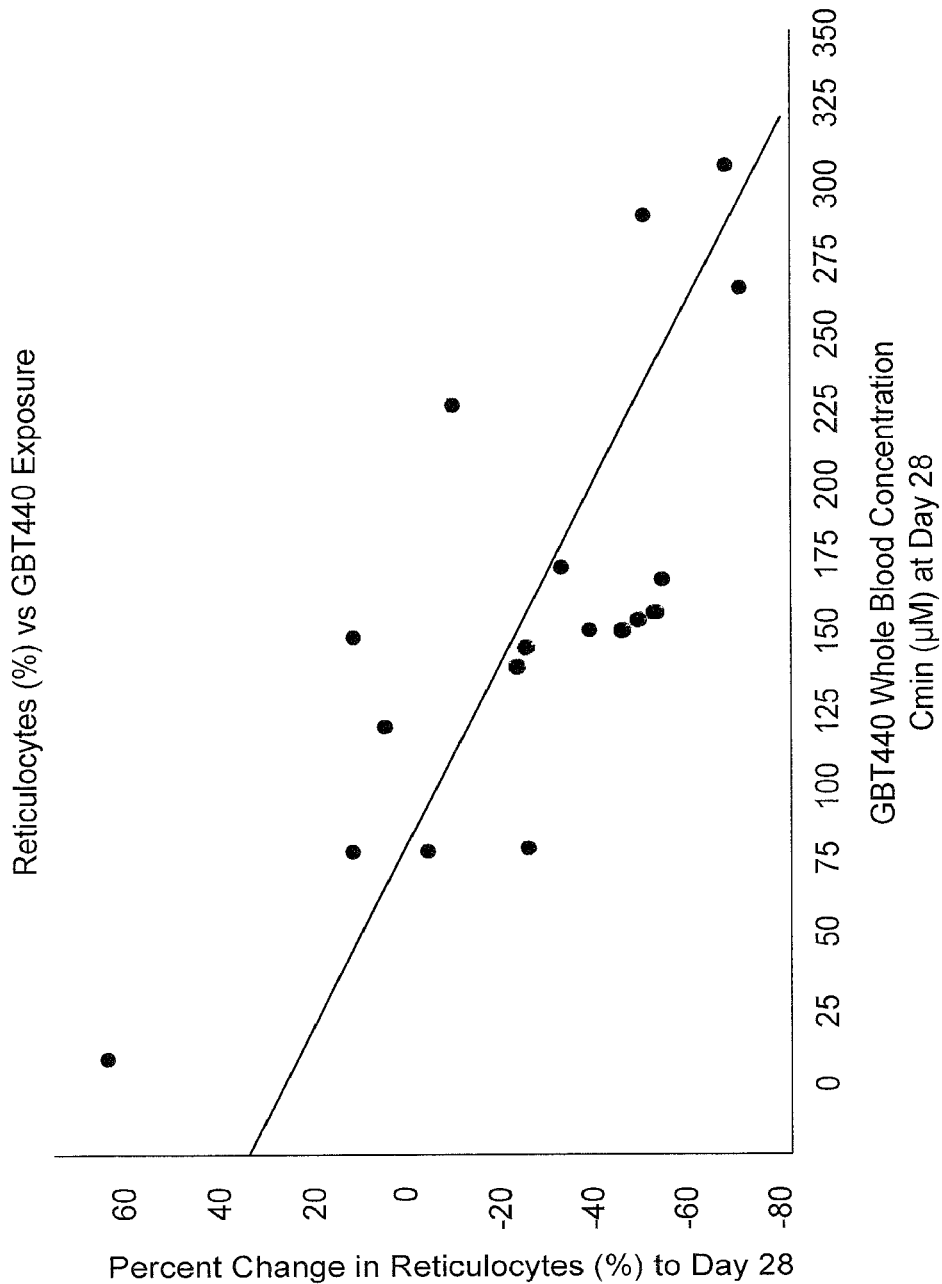

FIG. 8 illustrates the percent (%) change in reticulocytes to day 28 versus whole blood concentration of Compound 1.

Figure 9B:
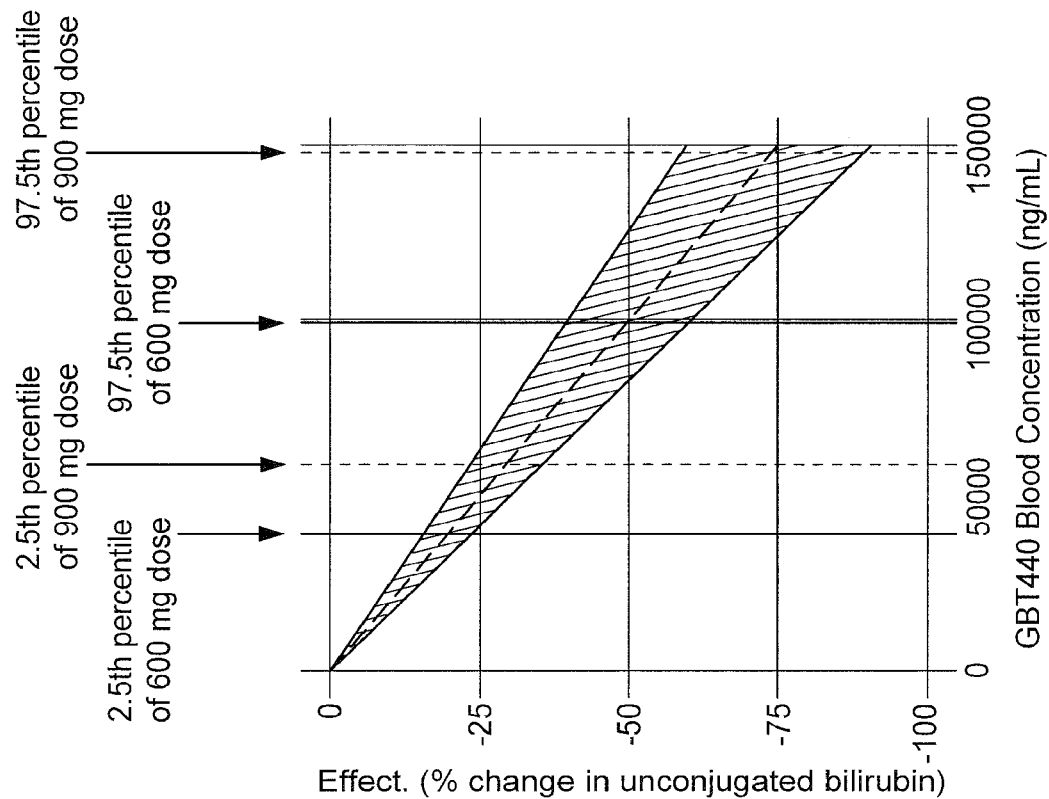
Figure 9A:
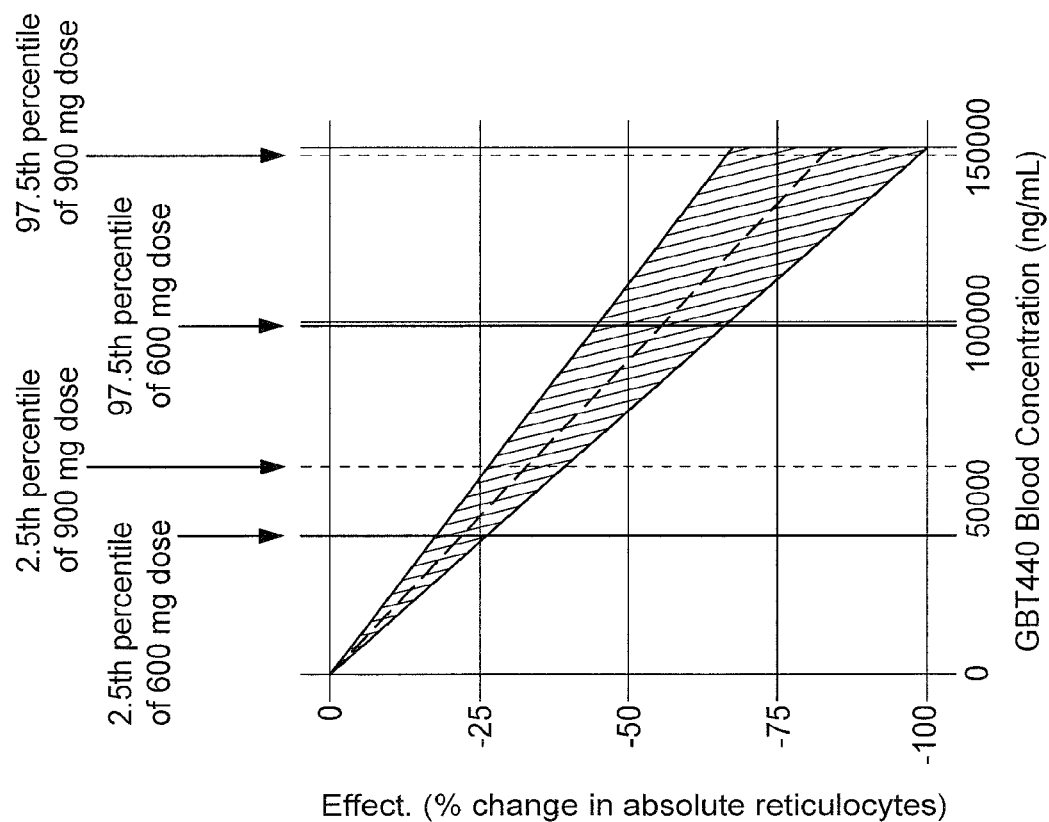
Figure 9D:
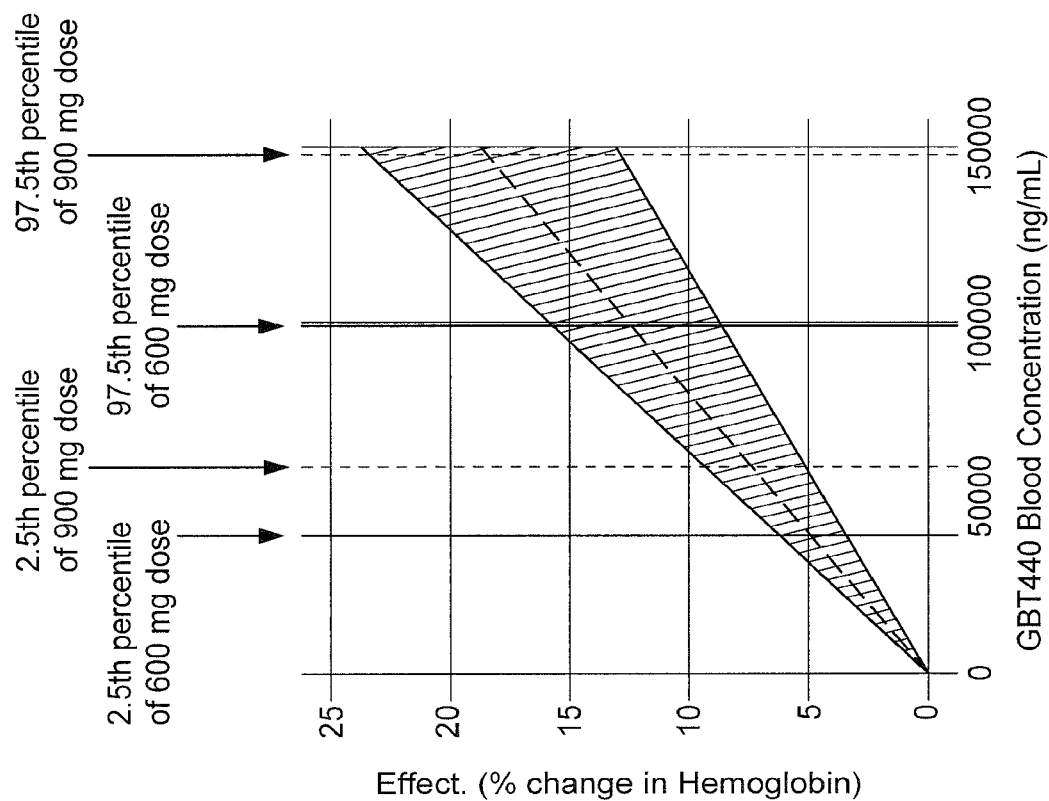
Figure 9C:
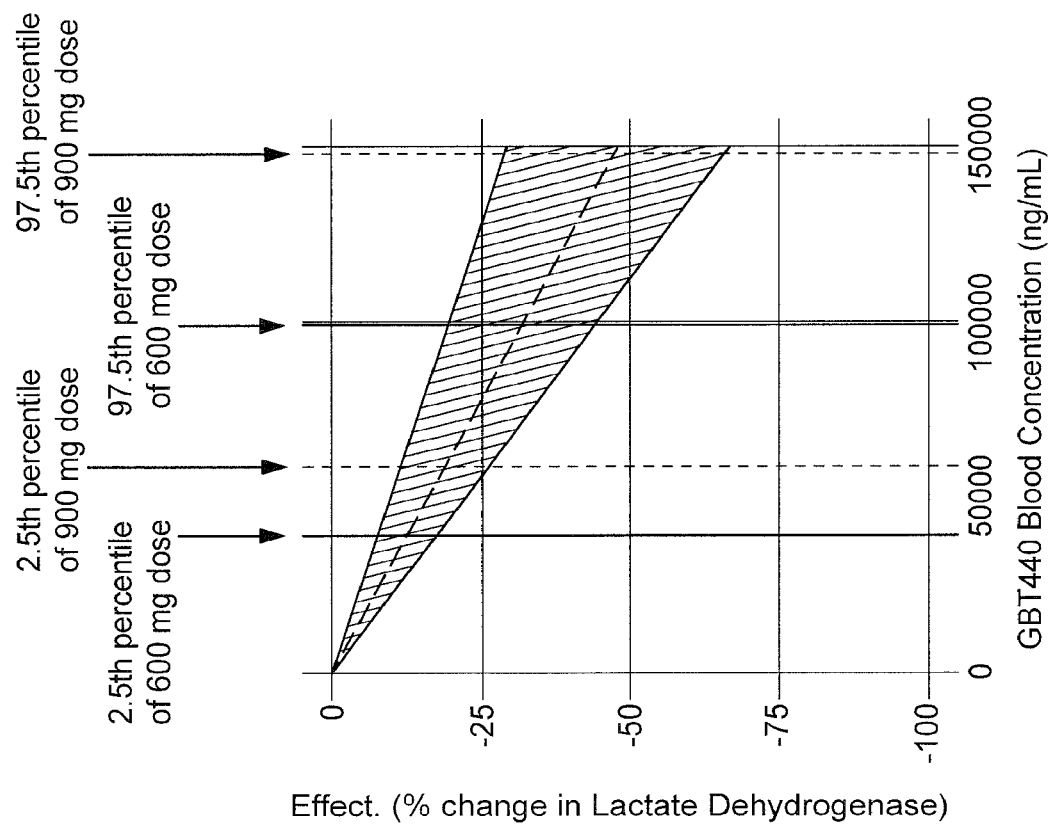

FIGS. 9A-9D illustrate the linear relationship between Compound 1 whole blood concentrations and effect on hemolytic measures: FIG. 9A shows percent (%) change in absolute reticulocytes; FIG. 9B shows percent (%) change in unconjugated bilirubin; FIG. 9C shows percent (%) change in LDH; and FIG. 9D shows percent (%) change in hemoglobin.

6. DETAILED DESCRIPTION OF THE INVENTION

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

6.1 Definitions

As used herein, the below terms have the following meanings unless specified otherwise.

It is noted here that as used in this specification and the appended claims, the singular forms "a," "an," and "the" and the like include plural referents unless the context clearly dictates otherwise.

The term "about" or "approximately" means an acceptable error for a particular value as determined by one of ordinary skill in the art, which depends in part on how the value is measured or determined. With regards to the dose, the term "about" or "approximately" means within 1, 2, 3, or 4 standard deviations. In certain embodiments, the term "about" or "approximately" means within 50%, 30%, 20%, 15%, 10%, 9%, 8%, 7%, 6%, 5%, 4%, 3%, 2%, 1%, 0.5%, or 0.05% of a given dose. In certain embodiments, the term "about" or "approximately" means within 50%, 20%, 15%, 10%, 9%, 8%, 7%, 6%, 5%, 4%, 3%, 2%, 1%, 0.5%, or 0.05% of a dose. In certain embodiments, the term "about" or "approximately" means within 0.5% to 1% of a given dose.

The term "administration" refers to introducing an agent into a patient. A therapeutic amount can be administered, which can be determined by the treating physician or the like. An oral route of administration is preferred. The related terms and phrases "administering" and "administration of", when used in connection with a compound or pharmaceutical composition (and grammatical equivalents), refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery to the patient of the drug.

The "crystalline ansolvate" of Compound 1 is a crystalline solid form of the free base of 2-hydroxy-6-((2-(1-isopropyl-1H-pyrazol-5-yl)pyridin-3-yl)methoxy)benzaldehyde, such as, e.g., crystalline Form I, Form II or Material N as disclosed in International Publication No. WO 2015/120133 A1 (see, e.g., pages 3-9 and pages 51-54), the disclosure of which is incorporated herein by reference in its entirety.

"Characterization" refers to obtaining data which may be used to identify a solid form of a compound, for example, to identify whether the solid form is amorphous or crystalline and whether it is unsolvated or solvated. The process by which solid forms are characterized involves analyzing data collected on the polymorphic forms so as to allow one of ordinary skill in the art to distinguish one solid form from other solid forms containing the same material. Chemical identity of solid forms can often be determined with solution-state techniques such as $^{13}$C NMR or $^{1}$H NMR. While these may help identify a material, and a solvent molecule for a solvate, such solution-state techniques themselves may not provide information about the solid state. There are, however, solid-state analytical techniques that can be used to provide information about solid-state structure and differentiate among polymorphic solid forms, such as single crystal X-ray diffraction, X-ray powder diffraction (XRPD), solid state nuclear magnetic resonance (SS-NMR), and infrared and Raman spectroscopy, and thermal techniques such as differential scanning calorimetry (DSC), solid state $^{13}$C-NMR, thermogravimetry (TG), melting point, and hot stage microscopy.

To "characterize" a solid form of a compound, one may, for example, collect XRPD data on solid forms of the compound and compare the XRPD peaks of the forms. For example, the collection of peaks which distinguish e.g., Form II from the other known forms is a collection of peaks which may be used to characterize Form II. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

An XRPD pattern is an x-y graph with diffraction angle (typically ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data:

different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2° 2θ to diffraction angles in XRPD patterns.

"Comprising" or "comprises" is intended to mean that the compositions and methods include the recited elements, but not exclude others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "dose" or "dosage" refers to the total amount of active material (e.g., Compound 1 disclosed herein) administered to a patient in a single day (24-hour period). The desired dose may be administered once daily, for example, as a single bolus. Alternatively, the desired dose may be administered in one, two, three, four or more subdoses at appropriate intervals throughout the day, where the cumulative amount of the subdoses equals the amount of the desired dose administered in a single day. The terms "dose" and "dosage" are used interchangeably herein.

The term "dosage form" refers to physically discrete units, each unit containing a predetermined amount of active material (e.g., Compound 1 disclosed herein) in association with the required excipients. Suitable dosage forms include, for example, tablets, capsules, pills, and the like.

The capsule of the present disclosure comprises excipients such as a pharmaceutically acceptable binder, filler (also known as diluent), disintegrant, and lubricant. Excipients can have two or more functions in a pharmaceutical composition. Characterization herein of a particular excipient as having a certain function, e.g., filler, disintegrant, etc., should not be read as limiting to that function. Further information on excipients can be found in standard reference works such as Handbook of Pharmaceutical Excipients, 3rd ed. (Kibbe, ed. (2000), Washington: American Pharmaceutical Association).

A "disintegrant" as used herein refers to an excipient that can breakup or disintegrate the formulation when it comes in contact with, for example, the gastrointestinal fluid. Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. In one embodiment, the disintegrant is carmellose sodium. In one embodiment, the disintegrant is powdered cellulose, microcrystalline cellulose, methylcellulose, or low-substituted hydroxypropylcellulose, or a combination thereof. In one embodiment, the disintegrant is carmellose, carmellose calcium, carmellose sodium or croscarmellose sodium, or a combination thereof. In one embodiment, the disintegrant is croscarmellose sodium.

Lubricants as used herein refers to an excipient that reduces friction between the mixture and equipment during granulation process. Exemplary lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. In one embodiment, the lubricant is stearic acid. In one embodiment, the lubricant is magnesium stearate. In one embodiment, the lubricant is magnesium stearate present in the amount of from about 0.5% to about 1.5% by weight of the formulation. In one embodiment, the lubricant is magnesium stearate.

In one embodiment, the lubricant is present at an amount of about: 0.5%, 0.75%, 1%, 1.25%, or 1.5 w/w. In another embodiment, the lubricant is present at an amount at an amount of about 0.5% w/w. In another embodiment, the lubricant is present at an amount at an amount of 0.5% w/w (±0.1%). In one embodiment, the lubricant is present at an amount of 0.5% w/w (±0.2%). In such embodiments, the lubricant can be magnesium stearate.

Binding agents or adhesives as used herein refer to an excipient which imparts sufficient cohesion to the blend to allow for normal processing operations such as sizing, lubrication, compression and packaging, but still allow the formulation to disintegrate and the composition to be absorbed upon ingestion. Exemplary binding agents and adhesives include, individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; and the like.

The binding agent(s) is present from about 2% to about 6%, by weight of the formulation. In one embodiment, the binding agent(s), is about 2%, 3%, 4%, 5%, or 6 w/w. In another embodiment, the binder is present at about 4% w/w of the formulation. In yet another embodiment, the binder is hypromellose.

Filler as used herein means an excipient that are used to dilute the compound of interest prior to delivery. Fillers can also be used to stabilize compounds because they can provide a more stable environment. Salts dissolved in buffered solutions (which also can provide pH control or maintenance) are utilized as diluents in the art, including, but not limited to a phosphate buffered saline solution. Fillers increase bulk of the composition to facilitate compression or create sufficient bulk for homogenous blend for capsule filling. Representative fillers include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. The filler(s) is present from about 6% to about 25%, by weight of the formulation. In one embodiment, the filler agent(s), is about 6%, 7%, 8%, 10%, 11%, 12%, 13%, 14%, 15%, 16%, 17%, 18%, 19%, 20%, 21%, 22%, 23%, 24%, or 25% w/w. In another embodiment, the composition comprises about 3.5% w/w or insoluble filler and about 2.5% w/w of soluble filler. In yet another embodiment, the insoluble filler is microcrystalline cellulose and the soluble filler is lactose.

As defined herein, where the mass of a compound is specified, for example, "500 mg of compound (1)," that amount refers to the mass of compound (1) in its free base form.

The term "hemoglobin" as used herein refers to any hemoglobin protein, including normal hemoglobin (Hb) and sickle hemoglobin (HbS).

The term "sickle cell disease" (SCD) or "sicke cell diseases" (SCDs) refers to one or more diseases mediated by sickle hemoglobin (HbS) that results from a single point mutation in the hemoglobin (Hb). Sickle cell diseases includes sickle cell anemia, sickle-hemoglobin C disease (HbSC), sickle beta-plus-thalassaemia (HbS/β) and sickle beta-zero-thalassaemia (HbS/β0).

"Substantially free" as used herein refers to ansolvate Form II of Compound 1 associated with <10% or Form I and/or Form N, preferably <5% Form I and/or Form N; and most preferably it shall refer to <2% Form I and/or Form N. Form I of Compound 1 is characterized by at least three X-ray powder diffraction peaks (Cu Kα radiation) at 12.82°, 15.74°, 16.03°, 16.63°, 17.60°, 25.14°, 25.82° and 26.44° 2θ (each ±0.2° 2θ); and Form N of Compound 1 is characterized by at least three X-ray powder diffraction peaks (Cu Kα radiation) at 11.65°, 11.85°, 12.08°, 16.70°, 19.65° and 23.48° 2θ (each ±0.2° 2θ).

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The full therapeutic effect does not necessarily occur by administration of one dose, and may occur only after administration of a series of doses and can be administered in one dose form or multiples thereof. For example, 600 mg of the drug can be administered in a single 600 mg capsule or two 300 mg capsules. Thus, a therapeutically effective amount may be administered in one or more administrations. For example, and without limitation, a therapeutically effective amount of an agent, in the context of treating disorders related to hemoglobin S, refers to an amount of the agent that alleviates, ameliorates, palliates, or eliminates one or more manifestations of the disorders related to hemoglobin S in the patient.

The term "pharmaceutically acceptable" refers to generally safe and non-toxic for in vivo, preferably human, administration.

"Subject" or "patient" refers to human.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition. For purposes of treatment of sickle cell disease, beneficial or desired clinical results include, but are not limited to, multilineage hematologic improvement, decrease in the number of required blood transfusions, decrease in infections, decreased bleeding, and the like. For purposes of treatment of interstitial pulmonary fibrosis, beneficial or desired clinical results include, but are not limited to, reduction in hypoxia, reduction in fibrosis, and the like.

6.2 Compounds and Uses

Compound 1 is 2-hydroxy-6-((2-(1-isopropyl-1h-pyrazol-5-yl)pyridin-3-yl)methoxy)benzaldehyde, having the formula:

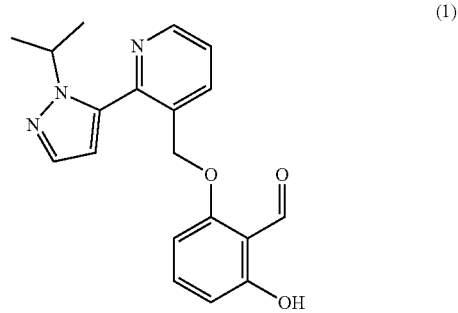 [SMILES: CC(C)n1nccc1-c1ncccc1COc1cccc(O)c1C=O]

(1)

(hereinafter "Compound 1" or GBT440, where the terms are used interchangeably), or a tautomer thereof.

Compound 1 can be prepared according to the methods described in, for example, International Publication Nos. WO 2015/031285 A1 (see, e.g., pages 14-17) and WO 2015/120133 A1 (see, e.g., pages 32-35), the disclosures of which are incorporated herein by reference in their entireties.

The free base of Compound 1 can be obtained as one or more crystalline forms, such as those described in, for example, International Publication Nos. WO 2015/031285 A1 (see, e.g., pages 19-24) and WO 2015/120133 A1 (see, e.g., pages 3-9 and 51-54), including Form II described below.

Form II

Figure 1:
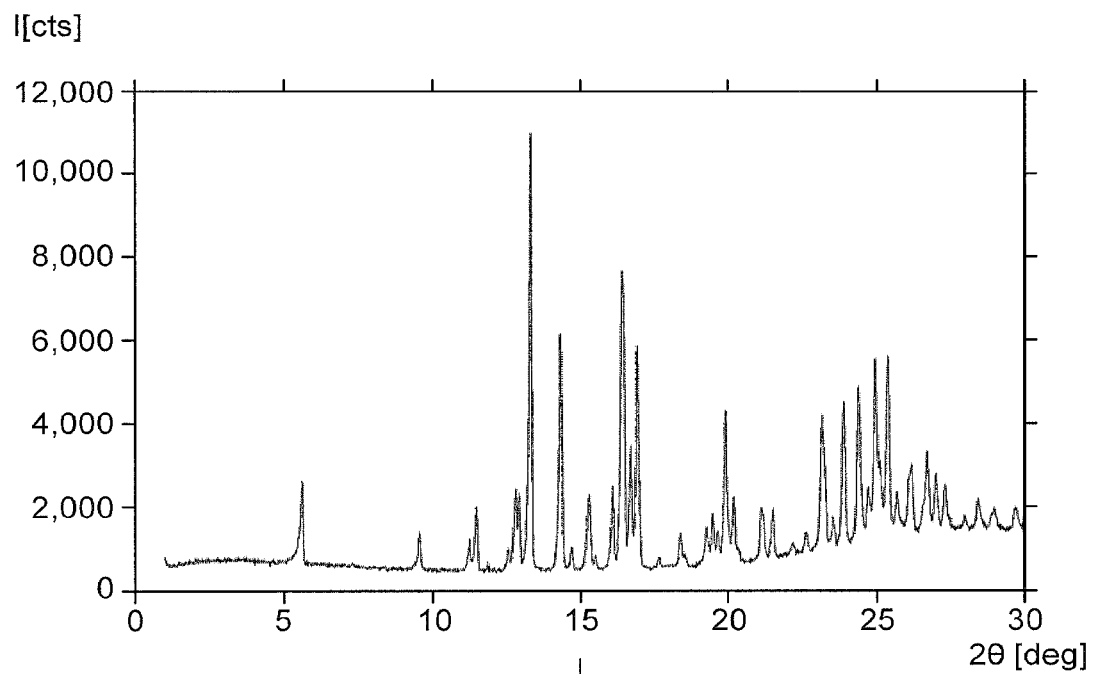
FIG. 1 is a XRPD profile and contemplated indexing for the free base Form II anhydrous crystal of Compound 1.

In addition to the XRPD provided above, the crystalline Compound 1 is characterized by an endothermic peak at (97±2) ° C. as measured by differential scanning calorimetry. In certain embodiments, the crystalline Form II of the free base of crystalline Compound 1 is characterized by the substantial absence of thermal events at temperatures below the endothermic peak at (97±2) ° C. as measured by differential scanning calorimetry. In certain embodiments, the crystalline Form II of the free base of crystalline Compound 1 is characterized by an X-ray powder diffraction peak (Cu Kα radiation at one or more of 13.37°, 14.37°, 19.95° or 23.92° 2θ. In certain embodiments, the crystalline ansolvate of the free base of crystalline Compound 1 is characterized by an X-ray powder diffraction peak (Cu Kα radiation at one or more of 13.37°, 14.37°, 19.95° or 23.92° 2θ. In certain embodiments, the crystalline Form II of the free base of crystalline Compound 1 is characterized by an X-ray powder diffraction pattern (Cu Kα radiation) substantially similar to that of FIG. 1. In certain embodiments, the crystalline ansolvate of the free base of crystalline Compound 1 is characterized by an X-ray powder diffraction pattern (Cu Kα radiation) substantially similar to that of FIG. 1.

In certain embodiments, the crystalline Form II of the free base of crystalline Compound 1 is characterized by at least one X-ray powder diffraction peak (Cu Kα radiation) selected from 13.37°, 14.37°, 19.95° and 23.92° 2θ (each ±0.2° 2θ). In certain embodiments, the crystalline Form II of the free base of crystalline Compound 1 is characterized by at least two X-ray powder diffraction peaks (Cu Kα radiation) selected from 13.37°, 14.37°, 19.95° and 23.92° 2θ (each ±0.2° 2θ). In certain embodiments, the crystalline Form II of the free base of crystalline Compound 1 is characterized by at least three X-ray powder diffraction peaks (Cu Kα radiation) selected from 13.37°, 14.37°, 19.95° and 23.92° 2θ (each ±0.2° 2θ).

In certain embodiments, the crystalline ansolvate of the free base of crystalline Compound 1 is characterized by at least one X-ray powder diffraction peak (Cu Kα radiation) selected from 13.37°, 14.37°, 19.95° and 23.92° 2θ (each ±0.2° 2θ). In certain embodiments, the crystalline ansolvate of the free base of crystalline Compound 1 is characterized by at least two X-ray powder diffraction peaks (Cu Kα radiation) selected from 13.37°, 14.37°, 19.95° and 23.92° 2θ (each ±0.2° 2θ). In certain embodiments, the crystalline ansolvate of the free base of crystalline Compound 1 is characterized by at least three X-ray powder diffraction peaks (Cu Kα radiation) selected from 13.37°, 14.37°, 19.95° and 23.92° 2θ (each ±0.2° 2θ).

In certain embodiments, the crystalline ansolvate of the free base of crystalline Compound 1 is substantially free of Form I and/or Form N; wherein Form I is characterized by at least three X-ray powder diffraction peaks (Cu Kα radiation) selected from 12.82°, 15.74°, 16.03°, 16.63°, 17.60°, 25.14°, 25.82° and 26.44° 2θ (each ±0.2° 2θ); and wherein Form N is characterized by at least three X-ray powder diffraction peaks (Cu Kα radiation) selected from 11.65°, 11.85°, 12.08°, 16.70°, 19.65° and 23.48° 2θ (each ±0.2° 2θ).

In certain embodiments, Form II is characterized by 1, 2, 3, 4, or more peaks as shown in Table 1 below.

TABLE 1

Observed peaks for Form II, XRPD file 613881.

| °2θ | d space (Å) | Intensity (%) |
|---|---|---|
| 5.62 ± 0.20 | 15.735 ± 0.581 | 24 |
| 12.85 ± 0.20 | 6.888 ± 0.108 | 22 |
| 12.97 ± 0.20 | 6.826 ± 0.106 | 21 |
| 13.37 ± 0.20 | 6.622 ± 0.100 | 100 |
| 14.37 ± 0.20 | 6.162 ± 0.087 | 56 |
| 15.31 ± 0.20 | 5.788 ± 0.076 | 21 |
| 16.09 ± 0.20 | 5.507 ± 0.069 | 23 |
| 16.45 ± 0.20 | 5.390 ± 0.066 | 69 |
| 16.75 ± 0.20 | 5.294 ± 0.064 | 32 |
| 16.96 ± 0.20 | 5.227 ± 0.062 | 53 |
| 19.95 ± 0.20 | 4.450 ± 0.045 | 39 |
| 20.22 ± 0.20 | 4.391 ± 0.043 | 20 |
| 23.18 ± 0.20 | 3.837 ± 0.033 | 38 |
| 23.92 ± 0.20 | 3.721 ± 0.031 | 41 |
| 24.40 ± 0.20 | 3.648 ± 0.030 | 44 |
| 24.73 ± 0.20 | 3.600 ± 0.029 | 22 |
| 24.99 ± 0.20 | 3.564 ± 0.028 | 50 |
| 25.12 ± 0.20 | 3.545 ± 0.028 | 28 |
| 25.39 ± 0.20 | 3.509 ± 0.027 | 51 |
| 25.70 ± 0.20 | 3.466 ± 0.027 | 21 |
| 26.19 ± 0.20 | 3.403 ± 0.026 | 27 |
| 26.72 ± 0.20 | 3.336 ± 0.025 | 30 |

TABLE 1-continued

Observed peaks for Form II, XRPD file 613881.

| °2θ | d space (Å) | Intensity (%) |
|---|---|---|
| 27.02 ± 0.20 | 3.300 ± 0.024 | 25 |
| 27.34 ± 0.20 | 3.262 ± 0.024 | 23 |
| 28.44 ± 0.20 | 3.138 ± 0.022 | 20 |

In certain embodiments, Compound 1 is used in the treatment of sickle cell disease, as described herein. In certain embodiments, a polymorph of Compound 1, as described in any of the embodiments provided herein, is used in the treatment of sickle cell disease. In certain embodiments, a polymorph of the free base of crystalline Compound 1, as described in any of the embodiments provided herein, is used in the treatment of sickle cell disease. In certain embodiments, the crystalline Form II of the free base of crystalline Compound 1, as described in any of the embodiments provided herein, is used in the treatment of sickle cell disease. In certain embodiments, the treatment is according to any of the pharmaceutical formulations, dosage forms, and/or dosage regimens as described herein. In certain embodiments, such treatment comprises administering to a subject or preparing for administration to such subject, 2-hydroxy-6-((2-(1-isopropyl-1H-pyrazol-5-yl) pyridin-3-yl)-methoxy)benzaldehyde, or a polymorph thereof, as described herein.

Accordingly, provided herein is a method for treating sickle cell disease in a patient comprising administering to the patient Compound 1. In certain embodiments, the compound is administered in a dose of from about 500 mg/day to about 1500 mg/day. In certain embodiments, the compound is administered in a dose of from about 600 mg/day to about 900 mg/day. In certain embodiments, the compound is administered in a dose of about 600 mg/day. In certain embodiments, the compound is administered in a dose of about 900 mg/day, or about 1200 mg/day, or about 1500 mg/day. In certain embodiments, the compound is administered in a dose of 600 mg/day. In certain embodiments, the compound is administered in a dose of 900 mg/day, 1200 mg/day or 1500 mg/day. In certain embodiments, the compound is administered once daily. In certain embodiments, the compound is a crystalline ansolvate form of Compound 1 as described in any of the embodiments provided herein.

Accordingly, also provided herein is Compound 1 for use in the treatment of sickle cell disease. In certain embodiments, about 900 mg/day to about 1500 mg/day of the compound is used for treatment. In certain embodiments, about 900 mg/day, about 1200 mg/day, or about 1500 mg/day of the compound is used for treatment. In certain embodiments, 900 mg/day, 1200 mg/day, or 1500 mg/day of the compound is used for treatment. In certain embodiments, the compound is used for treatment as a single dose. In certain embodiments, the compound is a crystalline ansolvate form of Compound 1 as described in any of the embodiments provided herein. In certain embodiments, the compound is prepared for use as a medicament, for example, a pharmaceutical formulation or dosage form, as described herein.

6.3 Pharmaceutical Formulations and Dosage Forms

In another aspect, Compound 1 is administered in a pharmaceutical formulation. Accordingly, provided herein are pharmaceutical formulations comprising a pharmaceutically acceptable excipient and a compound disclosed herein. In certain embodiments, the pharmaceutical formations comprise the crystalline free base ansolvate of Compound 1, including, for example, crystalline Form II. Suitable formulations are those described in, for example, International Publication No. WO WO 2015/031284 A1 (see, e.g., pages 18-21 and 28-29), the disclosure of which is incorporated herein by reference in its entirety.

Such formulations can be prepared for different routes of administration. Although formulations suitable for oral delivery will probably be used most frequently, other routes that may be used include intravenous, intramuscular, intraperitoneal, intracutaneous, and subcutaneous routes. Suitable dosage forms for administering any of the compounds described herein include tablets, capsules, pills, powders, parenterals, and oral liquids, including suspensions, solutions and emulsions. Sustained release dosage forms may also be used. All dosage forms may be prepared using methods that are standard in the art (see, e.g., Remington's Pharmaceutical Sciences, 16th ed., A. Oslo editor, Easton Pa. 1980). Because of their ease of administration, tablets and capsules represent the most advantageous oral dosage unit forms.

Pharmaceutically acceptable excipients are generally non-toxic, aid administration, and do not adversely affect the therapeutic benefit of Compound 1. Such excipients may be any solid, liquid, semi-solid or, in the case of an aerosol composition, gaseous excipient that is generally available to one of skill in the art. The pharmaceutical compositions disclosed herein are prepared by conventional means using methods known in the art.

The formulations disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

The amounts of active ingredients in a dosage form may differ depending on factors such as, but not limited to, the route by which it is to be administered to patients. In certain embodiments, the dosage forms provided herein comprise Compound 1 in an amount of about 10, about 20, about 30, about 40, about 50, about 100, about 150, about 200, about 250, about 300, about 400, or about 500 mg. In certain embodiments, the dosage forms provided herein comprise Compound 1 in an amount of about: 500, 550, 600, 650, 700, 750, 800, 850, 900, 950, 1000, 1050, 1100, 1150, 1200, 1250, 1300, 1350, 1400, 1450, or 1500 mg. In certain embodiments, the dosage forms provided herein comprise Compound 1 in an amount of about: 1050, 1100, 1150, 1200, 1250, 1300, 1350, 1400, 1450, or 1500 mg. In certain embodiments, the dosage forms provided herein comprise Compound 1 in an amount of about 50, about 100, or about 300 mg. In certain embodiments, the dosage forms provided herein comprise Compound 1 in an amount of about 300, about 600, about 900, about 1200, or about 1500 mg. In certain embodiments, the dosage forms provided herein comprise Compound 1 in an amount of 300 mg±10%. In certain embodiments, the dosage forms provided herein comprise Compound 1 in an amount of 300 mg±5%.

In one embodiment, provided is a capsule dosage form described in the Summary above (and embodiments thereof). The formulation in the capsule is prepared by wet granulation process as described below.

1. Dispensing

All the ingredients except the lubricant is screened through a 20-mesh screen to remove any agglomerates. The lubricant is screened through a 40-mesh screen.

2. High Shear Wet Granulation (HSWG) and Fluid Bed Drying

All the ingredients screened in the dispensing step except for the lubricant are added in a predefined order to the wet granulation bowl. The ingredients are mixed in the granulation bowl using the impellor only for a predetermined time to form a homogenous dry mixture. To the dry mix, water is used as a binding solution at a predetermined rate and amount while mixing using a high shear force with impellor and chopper at predetermined speeds. After adding the required amount of water, the wet granulation in kneaded or wet massed using both the impellor and chopper at predetermined speed and time. The wet granulation obtained is then transferred to the fluid bed dryer for drying. The granulation is dried until the desired dryness level is achieved measured by loss on drying (LOD)

3. Co-Milling or Sizing and Blending

The dried granulation from the HSWG and FBD step is then sized using a co-mill with a predetermined screen size and speed. A co-mill is used as a sizing step to ensure deagglomeration of large granule agglomerates and help achieve a uniform particle size distribution. The dried granules are then blended for a predetermined time in a V-blender along with the lubricant until a homogenous uniform blend is obtained. The final blend is then transferred to the encapsulation process.

4. Encapsulation, Packaging and Labeling

The final granulation blend is filled into capsules using either a semi-automatic/manual encapsulator or an automatic encapsulator depending on the scale and availability. A target weight of 350 mg of the granulation (containing 300 mg of API) is filled into each empty capsule to make 300 mg strength capsules. Filled capsules are polished followed by weight check and visual inspection for appearance to remove any defective capsules. Capsules are then packaged into 100 cc high-density polyethylene (HDPE) bottles at 30 capsules per bottle. The HDPE bottles are closed with child-resistant polypropylene (PP) screw caps with liner. Appropriate labels are applied over the HDPE bottles as per the regional regulations.

6.4 Capsule Dosage Forms

In certain embodiments, the capsule dosage form comprises:
(i) from about 65% to about 93% w/w of Compound 1 or a polymorph thereof; and
(ii) from about 2% to about 10% w/w a binder;

wherein w/w is relative to the total weight of the formulation (excluding the weight of the capsule). With regards to the capsule formulation; "about" means±10% of a given range or value.

In certain embodiments, the capsule dosage form further comprises from about 2% to about 10% a disintegrant.

In certain embodiments, the capsule dosage form further comprises from about 2% to about 10% a disintegrant and about 2% to 35% a filler.

In certain embodiments, the capsule dosage form comprises:
(i) from about 65% to about 86% w/w of Compound 1 or a polymorph thereof;
(ii) from about 2% to about 6% w/w a binder;
(iii) from about 6% to about 25% w/w a filler;
(iv) from about 2% to 6% w/w a disintegrant; and
(iv) from about 0.5% to about 1.5% w/w a lubricant;
wherein w/w is relative to the total weight of the formulation (excluding the weight of the capsule). With regards to the capsule formulation; "about" means±10% of a given range or value.

In certain embodiments, the capsule dosage form comprises:
(i) from about 65% to about 86% w/w of Compound 1 or a polymorph thereof;
(ii) from about 2% to about 6% w/w a binder;
(iii) from about 3.5% to about 25% w/w an insoluble filler or 2.5% to 25% w/w of soluble filler or 2.5% to 25% of a combination of soluble or insoluble filler;
(iv) from about 2% to about 6% w/w a disintegrant; and
(iv) from about 0.5% to about 1.5% w/w a lubricant.

In certain embodiments, the capsule dosage form comprises:
(i) about 86% w/w of Compound 1 or a polymorph thereof;
(ii) about 4% w/w a binder;
(iii) about 3.5% w/w an insoluble filler and 2.5% w/w of soluble filler;
(iv) about 3.5% w/w a disintegrant; and
(iv) about 0.5% w/w a lubricant.

In certain embodiments, the capsule dosage form comprises:
(i) 85.71% w/w of Compound 1 or a polymorph thereof;
(ii) 4% w/w a binder;
(iii) 3.64% w/w an insoluble filler and 2.65% w/w of soluble filler;
(iv) 2.65% w/w a disintegrant; and
(iv) 0.5% w/w a lubricant.

In certain embodiments:
Compound 1 is Form II substantially free of Form I and/or N;
the binder is hypromellose;
the insoluble filler is microcrystalline cellulose
the soluble filler is lactose monohydrate;
the disintegrant is croscarmellose sodium; and
the lubricant is magnesium stearate.

In certain embodiments, the capsule contains 300 mg of Compound 1 Form II substantially free of Form I and/or N.

In certain embodiments, Compound 1 is a crystalline ansolvate form. In one embodiment, the crystalline ansolvate is Form II characterized by at least one X-ray powder diffraction peak (Cu Kα radiation) selected from 13.37°, 14.37°, 19.95° and 23.92° 2θ (each ±0.2° 2θ). In one embodiment, the crystalline ansolvate is characterized by at least one X-ray powder diffraction peak (Cu Kα radiation) selected from 13.37°, 14.37°, 19.95° and 23.92° 2θ (each ±0.2° 2θ). In another embodiment, Form II is characterized by at least two X-ray powder diffraction peaks (Cu Kα radiation) selected from 13.37°, 14.37°, 19.95° and 23.92° 2θ (each ±0.2° 2θ). In another embodiment, the crystalline ansolvate is characterized by at least two X-ray powder diffraction peaks (Cu Kα radiation) selected from 13.37°, 14.37°, 19.95° and 23.92° 2θ (each ±0.2° 2θ). In yet another embodiment, Form II is characterized by at least three X-ray powder diffraction peaks (Cu Kα radiation) selected from 13.37°, 14.37°, 19.95° and 23.92° 2θ (each ±0.2° 2θ). In yet another embodiment, the crystalline ansolvate is characterized by at least three X-ray powder diffraction peaks (Cu Kα radiation) selected from 13.37°, 14.37°, 19.95° and 23.92° 2θ (each ±0.2° 2θ). In yet another embodiment, Form II is characterized by X-ray powder diffraction peaks (Cu Kα radiation) of 13.37°, 14.37°, 19.95° and 23.92° 2θ (each ±0.2° 2θ). In yet another embodiment, the crystalline ansolvate is characterized by X-ray powder diffraction peaks (Cu Kα radiation) of 13.37°, 14.37°, 19.95° and 23.92° 2θ (each ±0.2° 2θ). In yet another, Form II is characterized by an X-ray powder diffraction pattern (Cu Kα radiation) substantially similar to that of FIG. 1. In yet another, the crystalline ansolvate is characterized by an X-ray powder diffraction pattern (Cu Kα radiation) substantially similar to that of FIG. 1.

In certain embodiments, the capsule contains 300 mg±5% of Compound 1, wherein compound 1 is a crystalline ansolvate form that is characterized by at least two X-ray powder diffraction peaks (Cu Kα radiation) selected from 13.37°, 14.37°, 19.95° and 23.92° 2θ (each ±0.2° 2θ); wherein the crystalline ansolvate form is substantially free of Form I and/or N; wherein Form I is characterized by at least three X-ray powder diffraction peaks (Cu Kα radiation) selected from 12.82°, 15.74°, 16.03°, 16.63°, 17.60°, 25.14°, 25.82° and 26.44° 2θ (each ±0.2° 2θ); and wherein Form N is characterized by at least three X-ray powder diffraction peaks (Cu Kα radiation) selected from 11.65°, 11.85°, 12.08°, 16.70°, 19.65° and 23.48° 2θ (each ±0.2° 2θ).

6.5 Dosages

The dose of the compounds disclosed herein to be administered to a patient can be subject to the judgment of a health-care practitioner. Doses of the compounds disclosed herein vary depending on factors such as: specific indication to be treated, prevented, or managed; age and condition of a patient; and amount of second active agent used, if any.

In certain embodiments, the compound (e.g., Compound 1) is administered in a dose of from about 500 mg/day to about 1500 mg/day. In one embodiment the compound is administered in a dose of about 1100, about 1200, about 1300, about 1400, or about 1500 mg/day. In certain embodiments, the compound is administered in a dose of about is administered in a dose of about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg/day. In certain embodiments, the compound is administered in a dose of about 1050, about 1100, about 1150, about 1200, about 1250, about 1300, about 1350, about 1400, about 1450, or about 1500 mg/day. In certain embodiments, the compound is administered in a dose of about 500, about 550, about 600, about 650, about 700, about 750, about 800, about 850, about 900, about 950, or about 1000 mg/day. In certain embodiments, the compound is administered in a dose of about 600, about 650, about 700, about 750, about 800, about 850, or about 900 mg/day. In certain embodiments, the compound is administered in a dose of from about 500 mg/day to about 900 mg/day. In certain embodiments, the compound is administered in a dose of from about 600 mg/day to about 900 mg/day. In certain embodiments, the compound is administered in a dose of about 700 mg/day. In certain embodiments, the compound is administered in a dose of about 600 mg/day. In certain embodiments, the compound is administered in a dose of about 900 mg/day. In certain embodiments, the compound is administered in a dose of about 1200 mg/day. In certain embodiments, the compound is administered in a dose of about 1500 mg/day.

In certain embodiments, the compound (e.g., Compound 1) is administered as mg/Kg body weight of the patient, for example, from about 5 to about 50 mg/Kg body weight of the patient being treated/day, from about 10 to about 40 mg/Kg/day, from about 15 to about 30 mg/Kg/day, from about 15 to about 25 mg/Kg/day, about 5 to about 10 mg/Kg/day, about 10 to about 15 mg/Kg/day, about 15 to about 20 mg/Kg/day, about 20 to about 25 mg/Kg/day, about 25 to about 30 mg/Kg/day, about 30 to about 40 mg/Kg/day, or about 40 to about 50 mg/Kg/day.

The dose may be administered as a single bolus, or in one, two, three, four or more subdoses at appropriate intervals throughout the day. For example, if the dose to be administered is 900 or 1500 mg/day, the entire 900 or 1500 mg, respectively, may be administered at the same time. Alternatively, the 900 mg dose may be administered as, for example, three separate subdoses of 300 mg, where the first subdose is administered in the morning, the second subdose is administered in the afternoon of the same day, and the third subdose is administered in the evening of the same day, such that the cumulative amount administered for the day is 900 mg.

7. EXAMPLES

Certain embodiments disclosed herein are illustrated by the following non-limiting examples.

7.1 Example 1

The following example presents a Phase I randomised, placebo-controlled, double-blind, single and multiple ascending dose study of the tolerability and pharmacokinetics of Compound 1 (GBT440) in healthy subjects and patients with Sickle Cell Disease.

Objectives:
Primary Outcome Measures:
Safety, as assessed by frequency and severity of adverse events (AEs), and changes in vital signs, 12-lead electrocardiograms (ECGs), and laboratory assessments as compared to baseline [Time Frame: 30 days]
Secondary Outcome Measures:
Blood and plasma area under the concentration time curve (AUC) of GBT440 [Time Frame: 30 days]
Blood and plasma maximum concentration (Cmax) of GBT440 [Time Frame: 30 days]
Blood and plasma time to maximum concentration (Tmax) of GBT440 [Time Frame: 30 days]
Percentage of hemoglobin occupied or modified by GBT440 [Time Frame: 30 days]
Change from baseline in heart rate and pulse oximetry following exercise testing in healthy volunteers [Time Frame: 30 days]
Other Outcome Measures:
Percentage of sickled cells under ex vivo conditions [Time Frame: 30 days]
Effect of GBT440 on hemolysis as measured by LDH, direct bilirubin, hemoglobin, and reticulocyte count [Time Frame: 30 days]
Change from baseline in pain as measured by visual analog scale [Time Frame: 30 days]
Change from baseline in fatigue as measured by questionnaire [Time Frame: 30 days]
Exercise capacity as measured by 6-minute walk test [Time Frame: 30 days]
Methodology:
Experimental: GBT440
Subjects randomized 6:2 to receive daily oral dosing of GBT440 or placebo for 1 day (single dose) and up to 28 days (multiple dose)
Placebo Comparator: Placebo
Subjects randomized 6:2 to receive daily oral dosing of GBT440 or placebo for 1 day (single dose) and up to 28 days (multiple dose)
NUMBER OF SUBJECTS: 128
Criteria:
Inclusion Criteria:
Healthy male or female of non-child bearing potential; 18 to 55 years old; are non-smokers and have not used nicotine products within 3 months prior to screening.
Male or female, 18 to 60 years old, with sickle cell disease (hemoglobin SS) not requiring chronic blood transfusion therapy; without hospitalization in 30 days before screening or receiving blood transfusion within 30 days before screening; subjects are allowed concomitant use of hydroxyurea if the dose has been stable for the 3 months prior to screening.
Exclusion Criteria:
Subjects who have a clinically relevant history or presence of respiratory, gastrointestinal, renal, hepatic, haematological, lymphatic, neurological, cardiovascular, psychiatric, musculoskeletal, genitourinary, immunological, dermatological, connective tissue diseases or disorders.
Subjects who consume more than 14 (female subjects) or 21 (male subjects) units of alcohol a week.
Subjects who have used any investigational product in any clinical trial within 90 days of admission or who are in extended follow-up.
Healthy subjects who have used prescription drugs within 4 weeks of first dosing or have used over the counter medication excluding routine vitamins within 7 days of first dosing.
Subjects with sickle cell disease who smoke >10 cigarettes per day; have hemoglobin level <6 mg/dL or >10 mg/dL at screening; have aspartate aminotransferase (AST), alanine aminotransferase (ALT), or alkaline phosphatase (ALK)>3× upper limit of normal reference range (ULN) at screening; have moderate or severe renal dysfunction
Test Product, Dose and Route of Administration:
Compound 1 oral capsules at 2 strengths (50 and 100 mg)
Doses: 300, 500, 600, 700, 900, or 1000 mg/day
Alternatively, the following Doses may also be used: 900, 1200, or 1500 mg/day.

7.2 Example 2

The following example presents pharmacokinetic results from the study as described in Example 1.

Analysis of whole blood was performed as follows. 50 µL of diluted whole blood was mixed with 20 µL of GBT1592 (GBT440-D7) solution in acetonitrile. 0.3 mL of 0.1M citrate buffer solution (pH 3) was added to the sample, and the sample mixed briefly by vortexing, followed by sonication for 10 minutes. 2.0 mL methyl tert butyl ether (MTBE) was added to the sample, and the sample was capped, and mixed thoroughly by vortexing at high speed for 20 minutes. The sample was then centrifuged at 3300 rpm at room temperature for 10 minutes. 0.2 mL of the clear organic layer of the centrifuged sample was then transferred to a clean 96-well 2-mL plate, and the solvent was evaporated to dryness. The dried extract was reconstituted in 0.2 mL of a mixture of acetonitrile/methanol/water/DMSO (225:25.0: 250:50.0) and mixed thoroughly. The resultant reconstituted extract was analyzed by liquid chromatography mass spectrometry (LCMS).

For the LCMS, a Sciex API 4000 LC-MS-MS was equipped with an HPLC column. The peak area of the m/z 338.1→158.1 GBT440 product ion was measured against the peak area of the m/z 345.2→159.1 GBT1592 (GBT440-D7) internal standard product ion.

The whole blood samples, obtained as described above, were analyzed for pharmacokinetic parameters and RBC: Plasma ratios, as follows.

Terminal half-life and other pharmacokinetic parameters were calculated using Phoenix WinNonlin software. Apparent terminal half-life ($t_{1/2}$) values were calculated as $\ln(2)/k$, where k is the terminal elimination rate constant which is obtained by performing a linear regression on the terminal phase of a plot of the natural logarithm (ln) of concentration versus time.

RBC:Plasma ratio was calculated using the equation below.

$$\frac{RBC}{PL} = \frac{\frac{BL}{PL} - (1 - Het)}{Het} \qquad \text{Equation 1}$$

In Equation 1, RBC is the concentration of GBT440 in the red blood cells; PL is the concentration of GBT440 in plasma obtained by analysis of plasma sample; BL is the concentration of GBT440 in whole blood obtained by analysis of whole blood sample; and Het is the hematocrit value.

Figure 2:
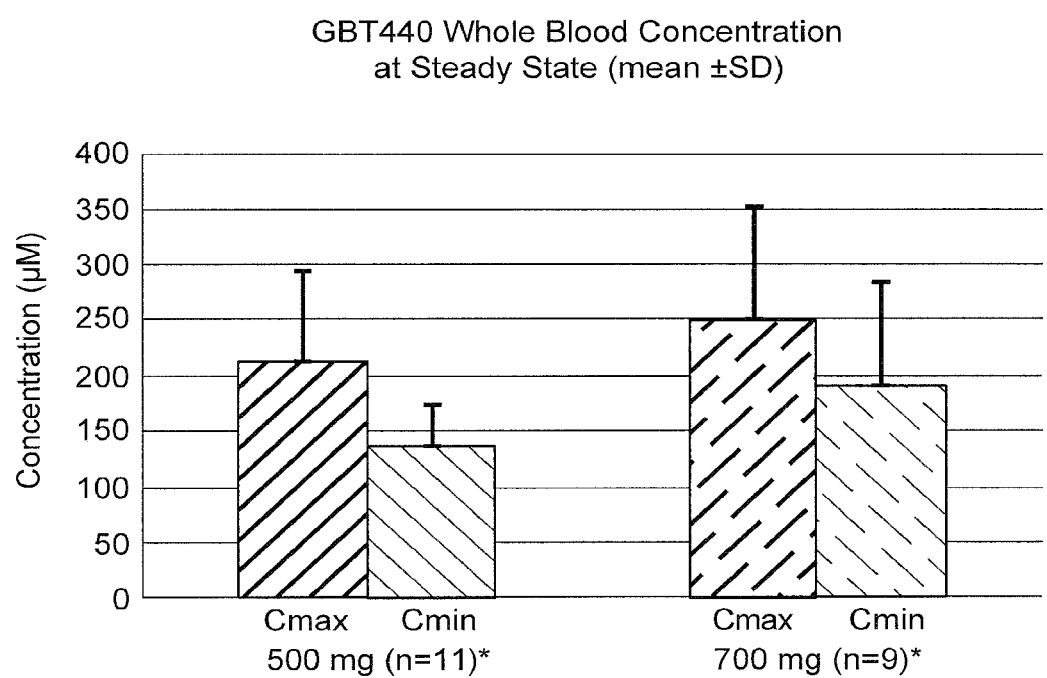
FIG. 2 illustrates whole blood concentration at steady state for two doses (500 mg, 700 mg) of Compound 1.

FIG. 2 illustrates representative whole blood concentrations at steady state for two doses (500 mg, 700 mg) of Compound 1 (GBT440)

A dose proportional increase in GBT440 was observed following single and multiple dosing. From these pharmacokinetic studies, the half-life of GBT440 in whole blood was determined to be approximately 3 days in healthy subjects, and 1.6 days in SCD subjects. In the tested subjects, the GBT440 RBC:plasma ratio was observed to be approximately 75:1. These pharmacokinetic results support once daily dosing.

7.3 Example 3

The following example presents hemoglobin oxygen equilibration results (e.g., oxygen equilibration curves) following dosing with Compound 1 (GBT440), from the study as described in Example 1.

Whole blood hemoximetry was used to measure oxygen equilibration. Blood from healthy volunteers and sickle cell disease (SCD) patients was drawn into 1.8 mL sodium citrate tubes. These samples were stored overnight at 4° C. prior to hemoximetry measurements. Based upon the hematocrit of the blood, either 50 μL or 100 μL of blood was diluted into 5 mL of 37° C. TES buffer (30 mM TES, 130 mM NaCl, 5 mM KCl, pH 7.4 at 25° C.). Diluted sample were loaded into TCS Hemox Analyzer cuvettes and oxygenated for twenty minutes using compressed air. After oxygenation, the samples were deoxygenated using nitrogen gas until the $pO_2$ reached 1.6 millimeters of mercury (mm Hg). Data during this deoxygenation step was collected into Oxygen Equilibrium Curve (OEC) files using the TCS Hemox Analytical Software (HAS). OEC files were then analyzed to obtain the p50 (the partial pressure of oxygen at which 50% of hemoglobin in a sample is saturated with $O_2$) and the p20 (the partial pressure of oxygen at which 20% of hemoglobin in a sample is saturated with $O_2$). Delta p20 values ($p20_{predose} - p20_{sample\ time}$) were then used to calculate the % Hb Modification.

Figure 3:
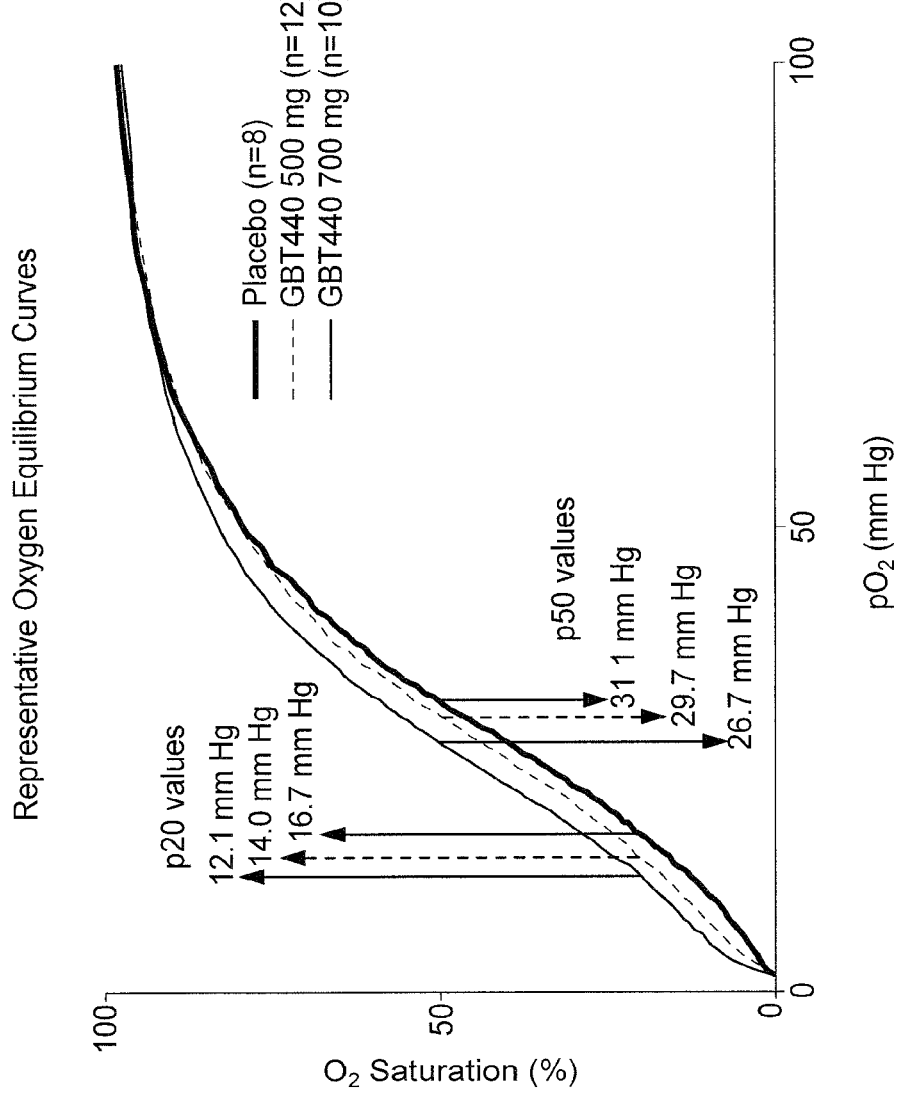
FIG. 3 illustrates representative oxygen equilibrium curves for two doses (500 mg, 700 mg) of Compound 1, with comparison to placebo.

FIG. 3 illustrates representative oxygen equilibrium curves for two doses (500 mg, 700 mg) of Compound 1 (GBT440), with comparison to placebo. As shown in this figure, administration of Compound 1 results in a left shift of the oxygen equilibrium curve: SCD subjects are right shifted; p50 shifts to normal range. As also shown in this figure, hemoglobin modification is proportional to dose.

7.4 Example 4

The following example presents results showing a change in hemoglobin over time following dosing with Compound 1 (GBT440), from the study as described in Example 1.

Figure 4:
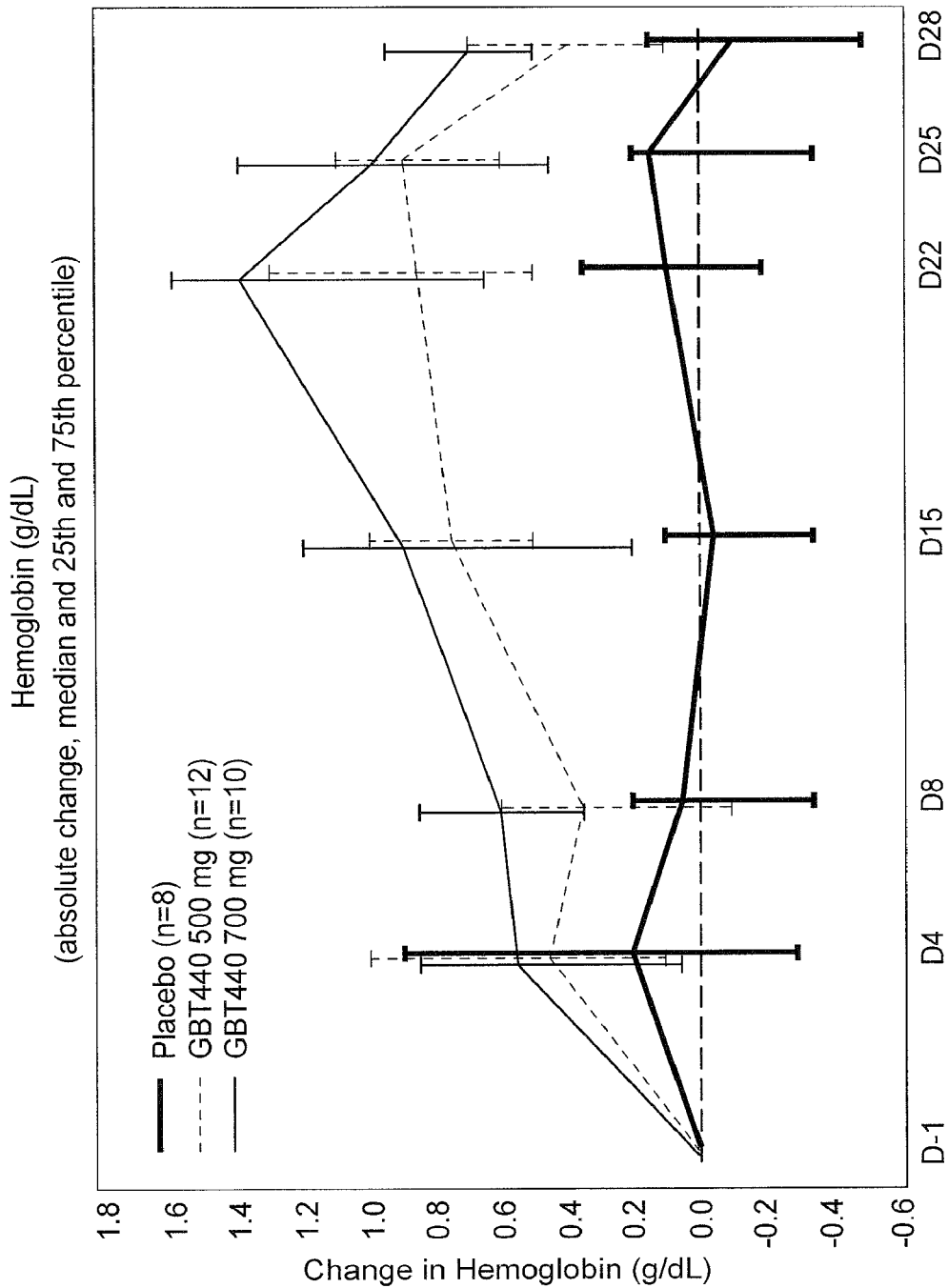
FIG. 4 illustrates change in hemoglobin (g/dL) over time for two doses (500 mg, 700 mg) of Compound 1, with comparison to placebo.

FIG. 4 illustrates the change in hemoglobin (g/dL) over time for two doses (500 mg, 700 mg) of Compound 1 (GBT440), with comparison to placebo. As shown in the figure, GBT 440 treatment led to a rapid and progressive rise in hemoglobin levels. The decline in later time points may be related to removal of dense cells and not related to return of hemolysis. The higher GBT440 dose level (700 mg) showed a trend for a better response compared to 500 mg. These results show that a reduction in hemolysis increases hemoglobin levels.

7.5 Example 5

The following example presents results showing a change in reticulocytes (e.g., percent change in reticulocytes) over time following dosing with Compound 1 (GBT440), from the study as described in Example 1.

Figure 5:
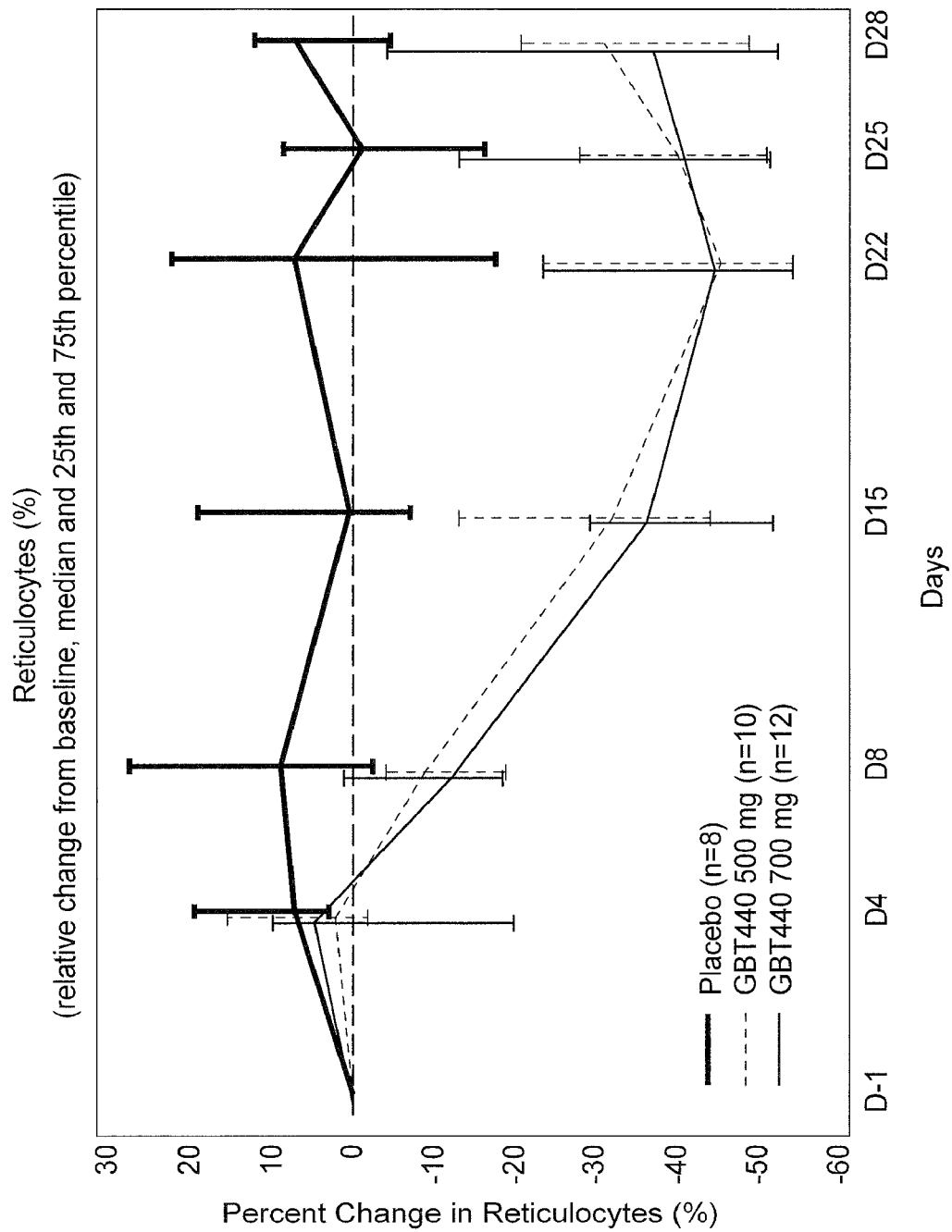
FIG. 5 illustrates percent (%) change in reticulocytes over time for two doses (500 mg, 700 mg) of Compound 1, with comparison to placebo.

FIG. 5 illustrates the percent (%) change in reticulocytes over time for two doses (500 mg, 700 mg) of Compound 1 (GBT440), with comparison to placebo. As shown in the figure, GBT 440 treatment led to a profound decline in reticulocytes, which is consistent with a reduction in hemolysis. The reduction in reticulocyte counts suggests improvement of red blood cell life span.

7.6 Example 6

The following example presents results showing a change in circulating sickle cells (e.g., percent change in circulating sickle cells) over time following dosing with Compound 1 (GBT440), from the study as described in Example 1.

Figure 6:
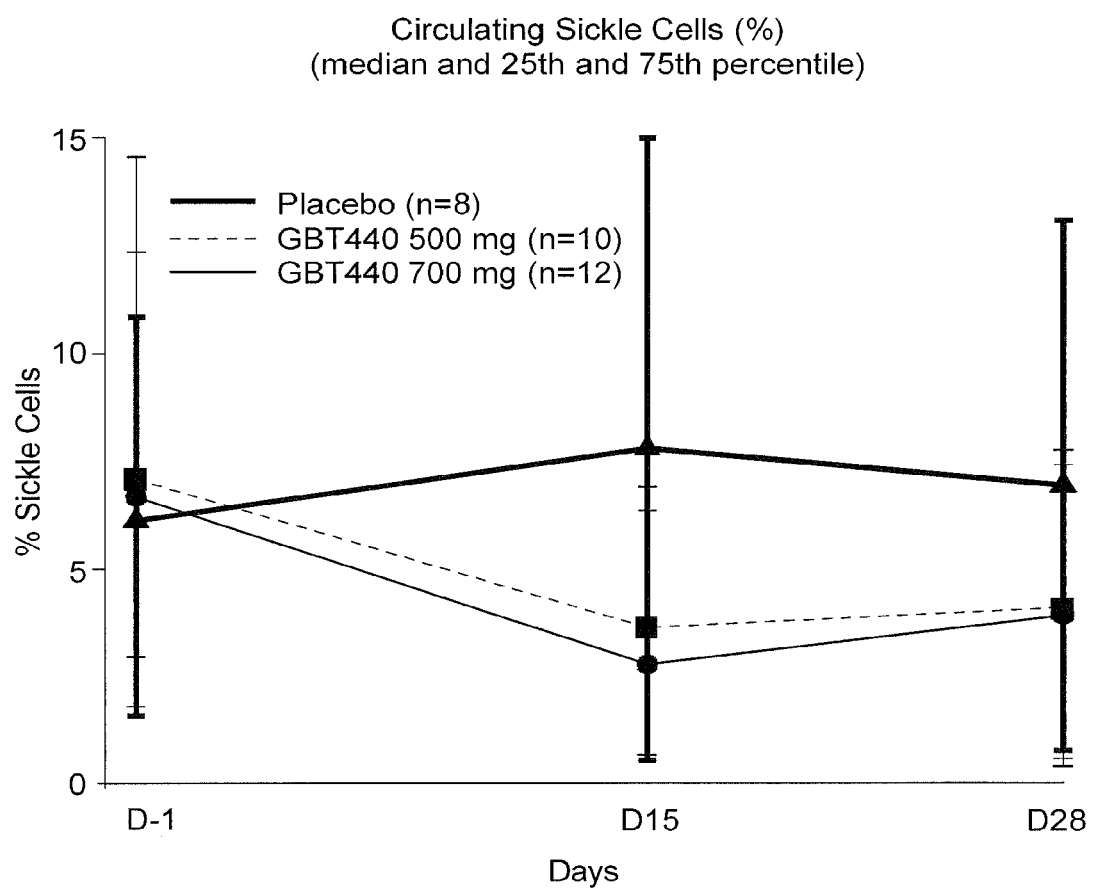
FIG. 6 illustrates percent (%) sickle cells over time for two doses (500 mg, 700 mg) of Compound 1, with comparison to placebo.

FIG. 6 illustrates percent (%) sickle cells over time for two doses (500 mg, 700 mg) of Compound 1 (GBT440), with comparison to placebo. As shown in the figure, baseline sickle cell counts were variable (1.1 to 19.4%). As also shown in the figure, GBT440 treatment reduced sickle cells in the peripheral blood which was sustained during the 28 day dosing period. These results show that a reduction in hemolysis increases hemoglobin levels.

This example also provides results showing a change in circulating sickle cells (e.g., percent change in circulating sickle cells) over time following dosing with Compound 1 (GBT440), from the study as described in Example 1.

To quantify irreversibly sickled cells (ISCs), six different fields were randomly selected and imaged at 40× magnification per slide. Each field contained 100 to 300 cells and >500 cells (in 3 or more fields) were counted per blood smear slide. Cells that were classically sickled shape or appeared linear (with length equal to or more than 3× the width) with irregular or pointed edges were counted as sickled. Elliptical red blood cells (also appearing linear but with length approximately twice the width) with smooth rounded edges were counted as normal. In general, isolated non-discoid cells with spiky turns were counted as sickled. Cells packed in a group that appeared non-discoid because of the packing were not counted as sickled since they demonstrate deformability by changing shape to accommodate the surrounding cells.

Morphological criteria for sickle cells included the following categories: (1) non-discoid irregular shaped cells with irregular or pointed edges; (2) elliptocytes with length more than twice the width and with irregular or pointed edges; and (3) irregular shaped elliptocytes.

FIGS. 7A and 7B provide representative images from a subject treated with 700 mg of Compound 1 (GBT440), over a period of one day as shown in FIG. 7A; and twenty-eight (28) days as shown in FIG. 7B. As shown in the figure, there is a marked reduction in sickle cells in peripheral blood smears.

7.7 Example 7

The following example presents results showing a change in reticulocytes at day 28, as a function of whole blood concentration of Compound 1 (GBT440), from the study as described in Example 1.

The strongest correlation between exposure and hematologic effect was observed with changes in reticulocyte counts (considered to be best biomarker for RBC survival).

FIG. 8 illustrates the percent (%) change in reticulocytes to day 28 versus whole blood concentration of Compound 1 (GBT440) (PK data from 500 and 700 mg dose levels; $R^2 \sim 0.56$). As shown in the figure, higher GBT440 exposures resulted in more profound reduction in reticulocyte counts.

The results provided in the above Examples 1-7 for Compound 1 (GBT440) demonstrate favorable pharmacokinetic data (e.g., long terminal t½), ex vivo anti-sickling activity, ability to increase hemoglobin levels, and ability to reduce reticulocyte counts. Further, the results provided in these Examples demonstrate that GBT440 whole blood concentrations were much higher than plasma concentrations (RBC:plasma ratio ~75:1), consistent with a high affinity and specificity of GBT440 for hemoglobin. These results supports the potential Compound 1 (GBT440) to be a beneficial therapeutic agent, suitable for once daily dosing at the disclosed doses, for the treatment of SCD.

7.8 Example 8

The following example presents response analysis of Compound 1 (GBT440) based on PK/PD modeling and hemolysis measures.

A PK/PD model was developed using PK and PD data from subjects with SCD, corresponding to Cohorts 11 (700 mg QD×28 days), 12 (500 mg QD×28 days) and 14 (500 mg BID×28 days) who participated in the study described in Example 1 above. The PK/PD model was developed to characterize the relationship between Compound 1 (GBT440) exposures, placebo and hemolysis measures (e.g., reticulocyte count, hemoglobin, unconjugated bilirubin and LDH). The drug effect was characterized using an indirect response model of drug/dose or concentration-dependent inhibition (e.g., bilirubin, reticulocytes, and LDH) or drug/dose or concentration-dependent stimulation (e.g., hemoglobin). Linear and non-linear models (maximal effect, e.g., $E_{max}$ model and sigmoidal $E_{max}$ model) were explored while the PK part of the model was kept fixed (e.g., sequential analysis). The PK/PD model used for hemolytic measures is shown in the equation below.

$$\frac{dA(1)}{dt} = k_{in} \times (1 - Sl \times WBC_{GBT440}) - k_{out} \times A(1) \quad \text{Equation 2}$$

where $$A(1)_{initial} = \text{Base} \quad \text{(Equation 3)}$$

In Equation 2, A(1) represents the amount of biomarker of interest; Sl represents the slope of the drug effect; $WBC_{GBT440}$ is the whole blood concentration of GBT440; and $k_{in}$ and $k_{out}$ are the production rate and the disappearance rate constant, respectively, of each biomarker.

The ratio of $k_{in}$ and/$c_{out}$ represents the baseline of the biomarker at steady state, as shown in the equation below.

$$\text{Base} = \frac{k_{in}}{k_{out}} \quad \text{Equation 4}$$

The final PK/PD relationship for the hemolysis markers was best described with an indirect response model where drug-related efficacy was driven by Compound 1 (GBT440) whole blood pharmacokinetics. Linear exposure response models were sufficient to characterize the data.

Based on this modeling, it was determined that the PD effects for the hemolysis measures (e.g., bilirubin, reticulocyte count, LDH and hemoglobin) are PK driven. FIGS. 9A-9B illustrate the linear relationship between Compound 1 whole blood concentrations and effect on hemolytic measures: FIG. 9A shows percent (%) change in absolute reticulocytes; FIG. 9B shows percent (%) change in unconjugated bilirubin; FIG. 9C shows percent (%) change in LDH; and FIG. 9D shows percent (%) change in hemoglobin. In the figure, the dashed line represents predicted change for a typical patient, the grey shaded area represents 95% CI (uncertainty in relationship), and the dotted lines represent $2.5^{th}$ and $97.5^{th}$ percentiles of the 600 mg and the 900 mg dose. The drug-related efficacy is a function of blood pharmacokinetics and the PD effects for the hemolysis measures disappear after dosing is stopped. A linear concentration-effect relationship was observed over the range of doses evaluated (500 mg to 1000 mg).

7.9 Example 9

The following example presents Hb occupancy analysis of Compound 1 (GBT440) based on population PK modeling. The following examples also presents simulated SCD measures outcomes.

Hb Modification (% Occupancy):

A population PK model was developed for Compound 1 (GBT440) based on data from healthy subjects and patients participating in the study as described in Example 1. The population PK model was developed to determine which doses would achieve Hb occupancy from 20% to 30%, which is the target range for therapeutic efficacy with Compound 1. The target range of 20% to 30% Hb modification is supported by treatment response data from the study. Participants who achieved >20% Hb occupancy showed an improved hematologic response compared to those who did not who achieve >20% Hb occupancy. Population PK models were developed for Compound 1 measured in plasma and in whole blood. Separate models were developed for patients and healthy subjects, as these populations appeared to show substantial differences in Compound 1 PK, due to the nature of SCD.

The percent Hb modification (% occupancy) was calculated according to Equations 5 and 6 below, where whole blood and plasma concentrations were derived from the population PK model, and hematocrit values (Hct) values were uniformly sampled from the range available in the database. A constant of 0.3374 was used in Equation 5 to convert RBC concentration from µg/mL into µM. In Equation 6, % occupancy was defined as the concentrations of Compound 1 in RBC (in µM) divided by the concentration of Hb in RBC (5000 µM) The models were used to evaluate the potential of several Compound 1 doses (e.g., 900 mg, 1200 and 1500 mg) to achieve the occupancy target of 20% to 30%.

$$RBC_{conc} = \frac{Blood_{conc} - [(1 - Het) \times Plasma_{conc}]}{Het} \times \frac{1}{0.3374} \quad \text{Equation 5}$$

$$\text{Calculated \% Occupancy} = \frac{RBC_{conc} \times 100}{1000 \times 5} \quad \text{Equation 6}$$

TABLE 2

Hb Occupancy Target for Compound 1 at doses of 900 mg and 1500 mg

|  | Dose of GBT440 | |
|---|---|---|
|  | 900 mg | 1500 mg |
| Estimated Hb Occupancy |  |  |
| Median % occupancy based on $C_{min}$ (2.5$^{th}$ to 97.5$^{th}$ percentiles) | 16 (7-31) | 26 (12-52) |

TABLE 2-continued

Hb Occupancy Target for Compound 1 at doses of 900 mg and 1500 mg

|  | Dose of GBT440 | |
|---|---|---|
|  | 900 mg | 1500 mg |
| Estimated Hb Occupancy |  |  |
| % Subjects with > 20% occupancy based on $C_{min}$ | 24.6% | 75.5% |

Values based on modeling of PK/PD data derived from the study as described in Example 1 and further simulations of such data.
Linear pharmacokinetics has been assumed for simulations of 1500 mg dose.

Additionally, determination of the estimated change from baseline in hemolysis measures for 900 mg and 1500 mg doses based on simulations (see Table 3 below) showed improvement over those observed in Cohorts 11, 12 and 14 (see Table 4 below).

TABLE 3

Simulated SCD Measures Outcomes (% Change from Baseline) for Compound 1 at doses of 900 mg and 1500 mg

|  | Compound 1 Doses | |
|---|---|---|
| Hemolysis Measure | 900 mg | 1500 mg |
| Bilirubin (%) | −47(33-62)$^a$ | −66 (51-78)$^a$ |
| Reticulocytes (%) | −54(28-78)$^a$ | −84 (61-94)$^a$ |
| LDH (%) | −30 (13-56)$^a$ | −64 (37-84)$^a$ |
| Hemoglobin (%) | 11.9 (6.7-21.1)$^b$ | $d$ |
| Hemoglobin (change from baseline) | 1.06 (0.60-1.9)$^c$ | $d$ |

Values represent median (2.5$^{th}$ to 97.5$^{th}$ percentiles)
$^a$Based on E$_{max}$ model. Note: An E$_{max}$ model was used to fit the hemolysis measures data. The E$_{max}$ model provided a similar fit to the bilirubin, reticulocytes and LDH data as the linear model, however it required E$_{max}$ value to be fixed to 100%, (these measures are decreasing over time). Since hemoglobin increases over time, the E$_{max}$ model was less robust than the linear model (Δ OFV > 25). Therefore predictions were not attempted for hemoglobin outside of the observed dose range (e.g. > 1000 mg).
$^b$Based on linear model
$^c$Based on a baseline Hb of 9 g/dL
$^d$ For hemoglobin measurements, the E$_{max}$ model resulted in a less reliable fit, with more uncertain estimates of E$_{max}$ and EC$_{50}$ (RSE > 100%), and therefore was not used to make predictions for the 1500 mg dose. The linear model was satisfactory describing the data in the observed dose range, however the linear model should not be used to extrapolate to higher doses, however, it can be assumed that treatment response of the higher dose (1500 mg) will be at least equal or higher compared to the lower dose (900 mg).

TABLE 4

Change from Baseline to Day 28 in Response Parameters in Subjects with SCD (Cohorts 11, 12, and 14)

|  | Change from Baseline to Day 28 Median (25$^{th}$, 75$^{th}$ percentile) | | | |
|---|---|---|---|---|
| Parameter | GBT440 500 mg (Cohort 12) n = 10 | GBT440 700 mg (Cohort 11) n = 12 | GBT440 1000 mg$^a$ (Cohort 14) n = 5 | Placebo (Pooled) n = 12 |
| Unconjugated bilirubin (%) | −30.6 (−48.9, −15.4) | −42.6 (−44.3, −23.8) | −56.3 (−57.8, −47.1) | 2.0 (−24.6, 9.9) |
| Reticulocytes (%) | −31.2 (−48.9, −20.8) | −37.0 (−52.6, −4.5) | −49.9 (−64.3, −34.4) | 9.0 (1.7, 13.8) |
| Hemoglobin (g/dL) | 0.4 (0.1, 0.7) | 0.7 (0.5, 1.0) | 0.0 (−0.4, 0.3) | −0.1 (−0.3, 0.4) |

TABLE 4-continued

Change from Baseline to Day 28 in Response Parameters in Subjects with SCD (Cohorts 11, 12, and 14)

| | Change from Baseline to Day 28 Median (25$^{th}$, 75$^{th}$ percentile) | | | |
|---|---|---|---|---|
| Parameter | GBT440 500 mg (Cohort 12) n = 10 | GBT440 700 mg (Cohort 11) n = 12 | GBT440 1000 mg$^a$ (Cohort 14) n = 5 | Placebo (Pooled) n = 12 |
| Lactate dehydrogenase (%) | −19.8 (−39.0, 6.2) | −11.9 (−30.1, −5.7) | −12.4 (−20.2, −12.2) | −4.8 (−13.1, −2.3) |
| Irreversibly sickled cells (%) | −56.4 (−70.2, −26.2) | −45.9 (−93.0, −6.0) | −45.7 (−57.9, 5.9) | 8.4 (−11.9, 16.8) |

$^a$500 mg twice daily
Source: Listing lb_2 for hemoglobin and Listing lb2_2 for LDH, bilirubin, and reticulocytes for 28-day data.
Sickled cells calculated internally.

The results of the modeling and simulations provided in the above Examples 8 and 9 for Compound 1 (GBT440) support the use of higher doses of Compound 1 (e.g., 900 mg, 1200 and 1500 mg) in the treatment of SCD.

7.10 Example 10

The following example describes the making of a Common Blend (CB) capsule formulation at 4.8 kg batch scale.

The CB capsule formulation at 300 mg strength was scaled up to 4.8 kg batch size and run under GMP conditions to manufacture clinical trial capsules of Form II of Compound 1 (GBT440). Per the process described stepwise, 4.114 kg of Form II of Compound 1 and the corresponding quantities of intragranular excipients excluding magnesium stearate were passed through a 20 mesh screen and added to a high shear granulator and blended for 5 minutes with impellor speed at 300 rpm. The premix was granulated by adding water at 60 g/min while mixing at high shear using impellor at 300 rpm and chopper at 1200 rpm. After addition of water, the wet granulation was further kneaded or wet massed for 3 min using impellor at 300 rpm and chopper at 1200 rpm. The wet granulation was dried using a fluid bed dryer at an inlet air temperature set at 55° C. and dried until the desired LOD (loss on drying) was attained. The dried granulation was passed through a co-mill at 1000 rpm to ensure breaking of large agglomerates and to attain a uniform particle size distribution.

Extragranular excipient (magnesium stearate) was passed through mesh #40 and blended with the granules for 3 minutes at 30 rpm in a V-blender.

Capsules were filled with the final blend using either an semiautomatic or manual encapsulator. The capsules had a an average fill of 350 mg granulation and final capsule weight of approximately 442 mg. 100% of the filled acceptable capsules were polished, weight sorted, visually inspected for any defects and passed through metal detection prior to packaging.

The capsules were tested by validated analytical methods meeting all product quality acceptance criteria, and released for human clinical use.

Quantitative compositions of exemplary 300 mg capsules are presented in Table 5, below.

TABLE 5

Quantitative Composition of Exemplary Compound 1, Form II Capsule (300 mg), indicating "Quantity" ((% w/w) and (mg/capsule)), "Function" and "Reference to Standard or Similar" for each component.

| Component | Quantity (% w/w) | Quantity (mg/capsule) | Function | Reference to Standard or Similar |
|---|---|---|---|---|
| Compound 1 Form II, Unmilled (intr agranular) | 85.71% | 300.00 | Drug substance | In-house |
| Hydroxypropyl methylcellulose (Methocel ® E5 Premium LV) (intragranular) | 4.00% | 14.00 | Binder | USP |
| Microcrystalline Cellulose (Avicel ® PH-101) (intragranular) | 3.64% | 12.74 | Filler | NF |
| Lactose Monohydrate (Foremost Grade 310) (intragranular) | 2.65% | 9.28 | Filler | NF |
| Croscarmellose Sodium (Ac-Di-Sol ®) (intragranular) | 3.50% | 12.25 | Disintegrant | Ph. Eur./NF |
| Sterile Water for Irrigation$^a$ | N/A | N/A | Granulation Liquid | USP |
| Magnesium Stearate (Hyqual ®, Vegetable Source) (extragranular) | 0.50% | 1.75 | Lubricant | NF |
| Total Fill Weight | 100.00% | 350.02 | | |

TABLE 5-continued

Quantitative Composition of Exemplary Compound 1, Form II Capsule (300 mg), indicating "Quantity" ((% w/w) and (mg/capsule)), "Function" and "Reference to Standard or Similar" for each component.

| Component | Quantity (% w/w) | Quantity (mg/capsule) | Function | Reference to Standard or Similar |
|---|---|---|---|---|
| HPMC (hydroxypropyl methylcellulose (hypromellose)), Swedish orange opaque, Vcaps ® Plus Coni-Snap, capsules, size 0 | N/A | 96.0 | Capsule shell | USP/NF, Ph. Eur. |
| Total Weight | N/A | 446.02 | | |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A capsule dosage form comprising:
(i) from about 65% to about 93% w/w of Compound 1;

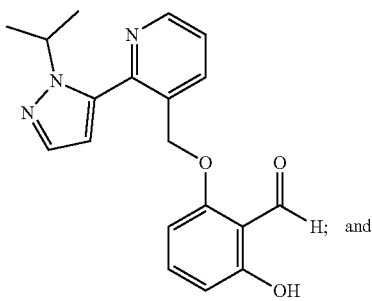

(ii) from about 2% to about 10% w/w a binder;
wherein w/w is relative to the total weight of the formulation, excluding the weight of the capsule, and
wherein the compound 1 is in a crystalline ansolvate form that is characterized by at least four X-ray powder diffraction peaks (Cu Kα radiation) at 13.37°, 14.37°, 19.95° and 23.92° 2θ, each peak is ±0.2° 2θ.

2. The capsule dosage form of claim 1, further comprising from about 2% to about 10% a disintegrant.

3. The capsule dosage form of claim 1, further comprising from about 2% to about 10% a disintegrant and about 2% to 35% a filler.

4. A capsule dosage form comprising:
(i) from about 65% to about 86% w/w of Compound 1;

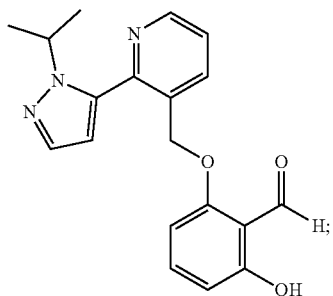

(ii) from about 2% to about 6% w/w a binder;
(iii) from about 6% to about 25% w/w a filler;
(iv) from about 2% to 6% w/w a disintegrant; and
(iv) from about 0.5% to about 1.5% w/w a lubricant;
wherein w/w is relative to the total weight of the formulation, excluding the weight of the capsule; and
wherein the compound 1 is in a crystalline ansolvate form that is characterized by at least four X-ray powder diffraction peaks (Cu Kα radiation) at 13.37°, 14.37°, 19.95° and 23.92° 2θ, each peak is ±0.2° 2θ.

5. The capsule dosage form of claim 4 comprising:
(i) from about 65% to about 86% w/w of the crystalline ansolvate form compound 1;
(ii) from about 2% to about 6% w/w a binder;
(iii) from about 3.5% to about 25% w/w an insoluble filler, or 2.5% to 25% w/w of soluble filler, or 2.5% to 25% of a combination of soluble or insoluble filler;
(iv) from about 2% to 6% w/w a disintegrant; and
(iv) from about 0.5% to about 1.5% w/w a lubricant.

6. The capsule dosage form of claim 5 comprising:
(i) about 86% w/w of the crystalline ansolvate form compound;
(ii) about 4% w/w a binder;
(iii) about 3.5% w/w an insoluble filler and 2.5% w/w of soluble filler;
(iv) about 3.5% w/w a disintegrant; and
(iv) about 0.5% w/w a lubricant.

7. The capsule dosage form of claim 6 comprising:
(i) 85.71% w/w of the crystalline ansolvate form compound;
(ii) 4% w/w a binder;
(iii) 3.64% w/w an insoluble filler and 2.65% w/w of soluble filler;
(iv) 2.65% w/w a disintegrant; and
(iv) 0.5% w/w a lubricant.

8. The capsule dosage form of claim 6 wherein:
the compound 1 is in a crystalline ansolvate form characterized by at least four X-ray powder diffraction peaks (Cu Kα radiation) at 13.37°, 14.37°, 19.950 and 23.92° 2θ, each peak is ±0.2° 2θ,
the binder is hypromellose;
the insoluble filler is microcrystalline cellulose;
the soluble filler is lactose monohydrate;
the disintregrant is croscarmellose sodium; and
the lubricant is magnesium stearate.

9. The capsule dosage form of claim 8, wherein the capsule contains 300 mg+/−5% of the crystalline ansolvate form compound; wherein the crystalline ansolvate form of compound 1 is substantially free of Form I and/or N; wherein Form I is characterized by at least three X-ray powder diffraction peaks (Cu Ka radiation) selected from 12.820, 15.740, 16.030, 16.630, 17.60°, 25.14°, 25.820 and 26.44020 (each X0.2 020); and wherein Form N is characterized by at least three X-ray powder diffraction peaks (Cu Ka radiation) selected from 11.650, 11.850, 12.080, 16.700, 19.650 and 23.48020 (each ±0.2 020).

10. A method for treating sickle cell disease in a patient comprising administering to the patient Compound 1:

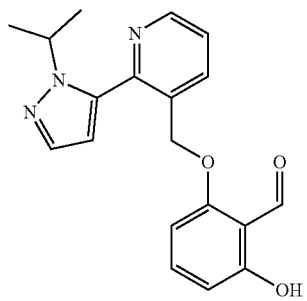

(I)

wherein Compound 1 is administered in a dose of about 500 mg/day to about 1500 mg/day; and
wherein the compound 1 is in a crystalline ansolvate form that is characterized by at least four X-ray powder diffraction peaks (Cu Kα radiation) at 13.37°, 14.37°, 19.95° and 23.92° 2θ, each peak is ±0.2° 2θ.

11. The method of claim 10, wherein the crystalline ansolvate form compound 1 is administered in a dose of from about 600 mg/day to about 900 mg/day.

12. The method of claim 10, wherein the crystalline ansolvate form compound 1 is administered in a dose of about 600 mg/day.

13. The method of claim 10, wherein the crystalline ansolvate form compound 1 is administered in a dose of about 900 mg/day, or about 1200 mg/day, or about 1500 mg/day.

14. The method of claim 10, wherein the crystalline ansolvate form compound 1 is administered in a dose of 600 mg/day.

15. The method of claim 10, wherein the crystalline ansolvate form compound 1 is administered in a dose of 900 mg/day, 1200 mg/day or 1500 mg/day.

16. The method of claim 10, wherein the crystalline ansolvate form compound 1 is administered once daily.

17. The method of claim 14, wherein the crystalline ansolvate form compound 1 is administered once daily.

18. The method of claim 15, wherein the crystalline ansolvate form compound 1 is administered once daily.

19. The method of claim 10, wherein the crystalline ansolvate form of Compound 1 is substantially free of Form I and/or Form N; wherein Form I is characterized by at least three X-ray powder diffraction peaks (Cu Ka radiation) selected from 12.820, 15.740, 16.030, 16.630, 17.600, 25.140, 25.820 and 26.44020 (each ±0.2 020); and wherein Form N is characterized by at least three X-ray powder diffraction peaks (Cu Ka radiation) selected from 11.65°, 11.850, 12.080, 16.700, 19.65" and 23.48° 20 (each ±0.2 20).

20. The method of claim 14, wherein the compound 1 is a crystalline ansolvate form that characterized by at least four X-ray powder diffraction peaks (Cu Ka radiation) at 13.370, 14.370, 19.950, and 23.92° 2θ, (each peak is ±0.2° 2θ).

21. The method of claim 20, wherein the crystalline ansolvate form of Compound 1 is substantially free of Form I and/or Form N; wherein Form I is characterized by at least three X-ray powder diffraction peaks (Cu Ka radiation) selected from 12.820, 15.740, 16.03°, 16.630, 17.600, 25.140, 25.820 and 26.44020 (each 0.2 020); and wherein Form N is characterized by at least three X-ray powder diffraction peaks (Cu Ka radiation) selected from 11.650, 11.85°, 12.08°, 16.700, 19.650 and 23.48020 (each ±0.2 020).

22. The method of claim 15, wherein the compound 1 is a crystalline ansolvate form that is characterized by at least four X-ray powder diffraction peaks (Cu Ka radiation) at 13.370, 14.370, 19.950, and 23.92° 2θ, (each peak is ±0.2° 2θ).

23. The method of claim 22, wherein the crystalline ansolvate form of Compound 1 is substantially free of Form I and/or Form N; wherein Form I is characterized by at least three X-ray powder diffraction peaks (Cu Ka radiation) selected from 12.820, 15.740, 16.03°, 16.630, 17.600, 25.140, 25.820 and 26.44020 (each ±0.2 020); and wherein Form N is characterized by at least three X-ray powder diffraction peaks (Cu Ka radiation) selected from 11.650, 11.850, 12.080, 16.700, 19.650 and 23.48020 (each ±0.2 020).

* * * * *